(12) United States Patent
Pagé et al.

(10) Patent No.: US 7,407,968 B2
(45) Date of Patent: Aug. 5, 2008

(54) COMPOUNDS

(75) Inventors: Daniel Pagé, Laval (CA); Christopher Walpole, Hudson (CA); Hua Yang, Montreal (CA)

(73) Assignee: AstraZeneca AB, Sodertalje (SE)

( * ) Notice: Subject to any disclaimer, the term of this patent is extended or adjusted under 35 U.S.C. 154(b) by 410 days.

(21) Appl. No.: 10/530,499

(22) PCT Filed: Oct. 15, 2003

(86) PCT No.: PCT/SE03/01604

§ 371 (c)(1),
(2), (4) Date: Apr. 6, 2005

(87) PCT Pub. No.: WO2004/035548

PCT Pub. Date: Apr. 29, 2004

(65) Prior Publication Data

US 2007/0105893 A1 May 10, 2007

(51) Int. Cl.
A01N 43/52 (2006.01)
A01N 43/42 (2006.01)
A61K 31/415 (2006.01)
A61K 31/44 (2006.01)
C07D 471/02 (2006.01)
C07D 491/02 (2006.01)
C07D 498/02 (2006.01)
C07D 235/00 (2006.01)

(52) U.S. Cl. .................. 514/303; 514/393; 514/394; 546/118; 548/304.4

(58) Field of Classification Search ............... 546/118; 548/304.4; 514/303, 393, 394
See application file for complete search history.

(56) References Cited

U.S. PATENT DOCUMENTS

| 2,945,044 | A | 7/1960 | Hoffmann et al. |
| 7,030,139 | B2 * | 4/2006 | Cheng et al. ............. 514/322 |
| 2006/0135554 | A1 | 6/2006 | Cheng et al. |

FOREIGN PATENT DOCUMENTS

| EP | 0445781 | 9/1991 |
| FR | 1481049 | 5/1967 |
| WO | WO 97/19063 | 5/1997 |
| WO | WO 00/46209 | 8/2000 |
| WO | WO 02/36590 | 5/2002 |
| WO | WO 02/060447 | 8/2002 |
| WO | 02/085866 | * 10/2002 |
| WO | WO 02/085866 | 10/2002 |
| WO | 03/053938 | * 7/2003 |
| WO | WO 2004/035548 | 4/2004 |

OTHER PUBLICATIONS

Mcpartland et al., The Journal of Comparative neurology, vol. 436, pp. 423-429.*
STN International, file CAPLUS, CAPLUS accession No. 1973:87, document No. 78:87, Paglietti G. et al, "Dialkylaminoalklybenzimidazoles of pharmacological interest", & Studi Sassaresi, Sezione 2: Archivio Bimestrale di Scienze Mediche e Naturali (1971), 49(5-6), 192-203.
Seki, T, et al., "2-Benzimidazolethiol derivatives . . . -5-substituted, benzimidazole", Chem. Abstracts, 1969, p. 445, vol. 71, No. 13, The Abstract, No. 61291h, Yakugaku Zasshi, 1969, 89 (5), 617-626.
Paglietti, G. et al., "Dialkylaminoalkylbenzimidazoles of pharmacological interest III", Chem. Abstracts, 1972, p. 479, vol. 77, No. 7, The Abstract, No. 48338h, Farmaco, Ed. Sci. 1972, 27 (4), 333-342.
Lecolier, S. et al., "New benzimidazoles with morphine activity", Chim. Ther., 1967, pp. 16-24, vol. 2, No. 1.
Burke, T. et al., "Probes for Narcotic Receptor Mediated Phenomena. 7.[1] Synthesis and Pharmacological Properties of Irreversible Ligands Specific for μ or δ Opiate Receptors", J. Med. Chem., 1984, pp. 1570-1574, vol. 27.
Smith, J. et al., "Necklace-Coded Polymer-Supported Combinatorial Synthesis of 2-Arylaminobenzimidazoles", J. Comb. Chem., 1999, pp. 368-370, vol. 1.
Monhemius et al., "CB1 Receptor Mediated Analgesia from the Nucleus Reticularis Gigantocellularis Pars Alpha is Activated in an Animal Model of Neuropathic Pain," Brain Research, 2001, vol. 908, pp. 67-74.

* cited by examiner

Primary Examiner—D. Margaret Seaman
Assistant Examiner—Niloofar Rahmani
(74) Attorney, Agent, or Firm—Jianzhong Shen

(57) ABSTRACT

Compounds of formula (I) wherein $R^{F1}$, $R^{F2}$, Z, $R^1$, $R^2$, Ar, X and Y are as defined in the specification as well as salts and pharmaceutical compositions including the compounds were prepared. These compounds are useful in therapy, in particular in the management of pain.

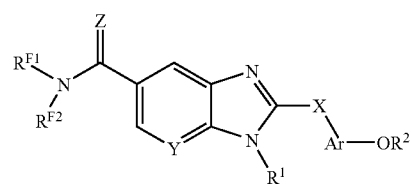

18 Claims, No Drawings

COMPOUNDS

CROSS-REFERENCE TO RELATED APPLICATIONS

This application is a US National Stage under 35 U.S.C § 371 of International Application No. PCT/SE2003/001604, filed on 15 Oct. 2003, which claims priority under 35 U.S.C. § 119(a)-(d) to Swedish Application No. 0203070-8 filed on 16 Oct. 2002.

BACKGROUND OF THE INVENTION

1. Field of the invention

The present invention relates to compounds that are therapeutic, and more particularly, to compounds that are effective in treating pain, cancer, multiple sclerosis, Parkinson's disease, Huntington's chorea and/or Alzheimer's disease.

2. Discussion of Relevant Technology

Pain management has been studied for many years. Cannabinoid receptor (e.g., $CB_1$ receptor, $CB_2$ receptor) ligands such as agonists, antagonists and inverse agonists may produce relief of pain in a variety of animal models by interacting with $CB_1$ and/or $CB_2$ receptors. Generally, $CB_1$ receptors are located predominately in the central nervous system, whereas $CB_2$ receptors are located primarily in the periphery and are primarily restricted to the cells and tissues derived from the immune system.

While $CB_1$ receptor agonists and mixed ($CB_1/CB_2$) receptor agonists, such as tetrahydrocannabinol (THC) and opiate drugs, are effective in anti-nociception models in animals, they tend to exert many undesired CNS side-effects, e.g., psychoactive side effects and the abuse potential of opiate drugs. These undesired CNS side effects are known to be mediated by the $CB_1$ receptors. In contrast, $CB_2$ receptor agonists may manage pain in humans or animals without causing those undesired CNS side effects due to the general location of $CB_2$ receptors and other factors.

Therefore, there is a need for $CB_2$ receptor ligands such as agonists useful in managing pain and/or treating other symptoms or diseases.

SUMMARY OF THE INVENTION

In one aspect, the invention provides a compound of formula (1) or pharmaceutically acceptable salts thereof:

(I)

wherein $R^{F1}$ and $R^{F2}$ are independently electron-withdrawing groups;

Z is selected from O= and S=;

$R^1$ is selected from $C_{1-10}$ alkyl; $C_{1-10}$ alkyl substituted by at least one of halogen, cyano, acetoxymethyl and nitro; $C_{2-10}$ alkenyl; $C_{2-10}$ alkenyl substituted by at least one of halogen, cyano, acetoxymethyl and nitro; $C_{2-10}$ alkynyl; $C_{2-10}$ alkynyl substituted by at least one of halogen, cyano, acetoxymethyl and nitro; $R^3R^4N$—$C_{1-6}$ alkyl; $R^3R^4NC(=O)$—$C_{1-6}$ alkyl; $R^3O$—$C_{1-6}$ alkyl; $R^3OC(=O)$—$C_{1-6}$ alkyl; $R^3C(=O)$—$C_{1-6}$ alkyl; $R^3C(=O)NR^3$—$C_{1-6}$ alkyl; $R^3R^4NSO_2$—$C_{1-6}R^3R^4C(=O)N(R^5)$—$C_{1-6}$ alkyl; $R^3R^4NSO_2N(R^5)$—$C_{1-6}$ alkyl; aryl-$C_{1-6}$ alkyl; aryl-$C(=O)$—$C_{1-6}$ alkyl; heterocyclyl-$C_{1-6}$ alkyl; heterocyclyl-$C(=O)$—$C_{1-6}$ alkyl; substituted aryl-$C_{1-6}$ alkyl; substituted aryl-$C(=O)$—$C_{1-6}$ alkyl; substituted heterocyclyl-$C_{1-6}$ alkyl; substituted heterocyclyl-$C(=O)$—$C_{1-6}$ alkyl; and $C_{1-10}$ hydrocarbylamino;

$R^2$ is selected from $C_{1-6}$ alkyl, substituted $C_{1-6}$ alkyl, $C_{2-6}$ alkenyl, substituted $C_{1-6}$ alkenyl, $C_{1-6}$ alkynyl, substituted $C_{2-6}$ alkynyl, $C_{3-6}$ cycloalkyl, substituted $C_{3-6}$ cycloalkyl, aryl, substituted aryl, and $C_{5-6}$ heteroaryl, and substituted $C_{5-6}$ heteroaryl;

$R^3$, $R^4$ and $R^5$ are independently selected from —H, $C_{1-6}$ alkyl, $C_{2-6}$ alkenyl, $C_{2-6}$ alkynyl, and a divalent $C_{1-6}$ group that together with another divalent $C_{1-6}$ group forms a portion of a ring;

X is a $C_{1-10}$ divalent group that separates groups connected thereto by one or two atoms;

Ar is a $C_{4-12}$ divalent aromatic group; and

Y is selected from —CH= and —N=.

Another aspect of the invention is the use of the compound of the invention as a medicament.

A further aspect of the invention is to use the compound of the invention in the treatment of pain, cancers, multiple sclerosis, Parkinson's disease, Huntington's chorea and/or Alzheimer's disease.

In a further aspect, the present invention provides a pharmaceutical composition comprising a compound of the invention and a pharmaceutically acceptable carrier.

In a further aspect, the present invention provides a method for the therapy of pain in a warm-blooded animal, comprising: administering to said animal in need of such therapy a therapeutically effective amount of a compound of the invention.

In a further aspect, the present invention provides a method of producing a compound comprising: reacting a compound represented by formula (II) with $R^2OArXCOA$:

(II)

wherein $R^{F1}$ and $R^{F2}$ are independently electron-withdrawing groups;

Z is selected from O= and S=;

$R^1$ is selected from $C_{1-10}$ alkyl; $C_{1-10}$ alkyl substituted by at least one of halogen, cyano, acetoxymethyl and nitro; $C_{2-10}$ alkenyl; $C_{2-10}$ alkenyl substituted by at least one of halogen, cyano, acetoxymethyl and nitro; $C_{2-10}$ alkynyl; $C_{2-10}$ alkynyl substituted by at least one of halogen, cyano, acetoxymethyl and nitro; $R^3R^4N$—$C_{1-6}$ alkyl; $R^3R^4NC(=O)$—$C_{1-6}$ alkyl; $R^3O$—$C_{1-6}$ alkyl; $R^3OC(=O)$—$C_{1-6}$ alkyl; $R^3C(=O)$—$C_{1-6}$ alkyl; $R^3C(=O)NR^3$—$C_{1-6}$ alkyl; $R^3R^4NSO_2$—$C_{1-6}$ alkyl; $R^3CSO_2N(R^4)$—$C_{1-6}$ alkyl; $R^3R^4NC(=O)N(R^5)$—$C_{1-6}$ alkyl; $R^3R^4NSO_2N^5)$—$C_{1-6}$ alkyl; aryl-$C_{1-6}$ alkyl; aryl-$C(=O)$—$C_{1-6}$ alkyl; heterocyclyl-$C_{1-6}$alkyl; heterocyclyl-C(=O)—$C_{1-6}$alkyl; substituted aryl-$C_{1-6}$alkyl; substituted aryl-C(=O)—$C_{1-6}$alkyl; substituted heterocyclyl-$C_{1-6}$alkyl; substituted heterocyclyl-C(=O)—$C_{1-6}$alkyl; and $C_{1-10}$hydrocarbylamino;

$R^2$ is selected from $C_{1-6}$alkyl, substituted $C_{1-6}$alkyl, $C_{2-6}$alkenyl, substituted $C_{2-6}$alkenyl, $C_{2-6}$alkynyl, substituted $C_{1-6}$alkynyl, $C_{3-6}$cycloalkyl, substituted $C_{3-6}$cycloalkyl, aryl, substituted aryl, and $C_{5-6}$heteroaryl, and substituted $C_{5-6}$heteroaryl;

$R^3$, $R^4$ and $R^5$ are independently selected from —H, $C_{1-6}$alkyl, $C_{2-6}$alkenyl, $C_{2-6}$alkynyl, and a divalent $C_{1-6}$ group that together with another divalent $C_{1-6}$ group forms a portion of a ring;

X is a $C_{1-10}$ divalent group that separates groups connected thereto by one or two atoms;

A is selected from —H, —Cl, —Br, and —I;

Ar is a $C_{4-12}$ divalent aromatic group; and

Y is selected from —CH= and —N=.

In another aspect, the present invention provides a method of producing a compound comprising the step of reacting a compound represented by formula (III) with formaldehyde:

(III)

wherein r and s are selected from 0, 1 and 2;

$R^{10}$ is selected from $C_{1-6}$alkylene, —O—, and —$NR^{11}$—, wherein $R^{11}$ is a $C_{1-6}$alkyl;

$R^{F1}$ and $R^{F2}$ are independently electron-withdrawing groups;

X is a $C_{1-10}$ divalent group that separates groups connected thereto by one or two atoms;

Ar is a $C_{4-12}$ divalent aromatic group;

$R^2$ is selected from $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $C_{3-6}$cycloalkyl, substituted $C_{3-6}$cycloalkyl, aryl, substituted aryl, and $C_{5-6}$heteroaryl, and substituted $C_{5-6}$heteroaryl; and Y is selected from —CH= and —N=.

DESCRIPTION OF THE INVENTION

Accordingly, it is an objective of certain embodiments of the invention to provide a compound that is effective in managing pain without causing the side effects mentioned above.

It is another objective of certain embodiments of the invention to provide a compound that is a $CB_2$ receptor ligand such as a $CB_2$ agonist that may be useful in managing pain and/or treating other symptoms or diseases.

DEFINITIONS

Unless specified otherwise within this specification, the nomenclature used in this specification generally follows the examples and rules stated in *Nomentclature of Organic Chemistry*, Sections A, B, C, D, E, F, and H, Pergamon Press, Oxford, 1979, which is incorporated by references herein for its exemplary chemical structure names and rules on naming chemical structures.

"$CB_1/CB_2$ receptors" means $CB_1$ and/or $CB_2$ receptors.

The term "$C_{m-n}$," or "$C_{m-n}$ group" used alone or as a prefix, refers to any group having m to n carbon atoms.

The term "hydrocarbon" used alone or as a suffix or prefix, refers to any structure comprising only carbon and hydrogen atoms up to 14 carbon atoms. The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. Unless otherwise specified, "alkyl" general includes both saturated alkyl and unsaturated alkyl.

The term "alkylene" used alone or as suffix or prefix, refers to divalent straight or branched chain hydrocarbon radicals comprising 1 to about 12 carbon atoms, which serves to link two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms, wherein the radical is located on a carbon of the aromatic ring. For example, aryl may be selected from phenyl and naphthyl.

The term "non-aromatic group" or "non-aromatic" used alone, as suffix or as prefix, refers to a chemical group or radical that does not contain a ring having aromatic character (e.g., 4n+2 delocalized electrons).

The term "arylene" used alone or as suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to link two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings sharing two atoms therebetween. Heterocycle may have aromatic character or may not have aromatic character.

The term "heteroalkyl" used alone or as a suffix or prefix, refers to a radical formed as a result of replacing one or more carbon atoms of an alkyl with one or more heteroatoms selected from N, O, P and S.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group", "heterocyclic moiety," "heterocyclic," or "heterocycle" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen from a carbon of a ring of the heterocycle.

The term "heterocyclylene" used alone or as a suffix or prefix, refers to a divalent radical derived from a heterocycle by removing two hydrogens therefrom, which serves to link two structures together.

The term "heteroaryl" used alone or as a suffix or prefix, refers to a heterocyclyl having aromatic character, wherein the radical of the heterocyclyl is located on a carbon of an aromatic ring of the heterocyclyl.

The term "heterocycloalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-12}$hydrocarbon groups, or one or more chemical groups containing one or more heteroatoms selected from N, O, S, F, Cl, Br, I, and P. Exemplary chemical groups containing one or more heteroatoms include heterocyclyl, —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$—NRC(=O)R, oxo (=O), imino (=NR), thio (=S), and oximino (=N—OR), wherein each "R" is a $C_{1-12}$hydrocarbyl. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any suitable hydrogen on the phenyl ring.

Ring nitrogen atoms of five-membered heteroaryl, heterocyclyl or bicyclic heteroaryl may be unsubstituted or substituted, if such a substitution is chemically possible without quaternization of said ring nitrogen, preferably with moieties independently selected from the group consisting of $C_{1-6}$alkyl, and —C(=O)R, wherein R is a $C_{1-6}$alkyl.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

The term "optionally substituted" refers to both groups, structures, or molecules that are substituted and those that are not substituted.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofur, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

One type of polycyclic heterocycles is bicyclic heteroaromatic ring system. A bicyclic heteroaromatic ring system is a ring system having two five- or six-membered heteroaromatic rings, or a phenyl and a five- or six-membered heteroaromatic ring, or a phenyl and a heterocyclyl ring, or a five- or six-membered heteroaromatic ring and a heterocyclyl ring, connected by a ring fusion, said bicyclic heteroaromatic ring system comprising 8 to 12 ring atoms wherein 1, 2 or 3 of the ring atoms are independently selected from N, O and S.

For example, bicyclic heteroaromatic ring systems may be selected from indole, indoline, quinoline, tetrahydroquinoline, isoquinoline, tetrahydroisoquinoline, 1,4-benzodioxan, coumarin, dihydrocoumarin, benzofuran, 2,3-dihydrobenzofuran, 1,2-benzisoxazole, benzothiophene, benzoxazole, benzothiazole, benzimidazole, benzotriazole, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinolizidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula O—R, wherein —R is selected from a hydrocarbon radical. Exemplary alkoxy includes methoxy, ethoxy, propoxy, isopropoxy, butoxy, t-butoxy, isobutoxy, cyclopropylmethoxy, alkyloxy, and propargyloxy.

The term "aryloxy" used alone or as suffix or prefix, refers to radicals of the general formula —O—Ar, wherein —Ar is an aryl.

The term "heteroaryloxy" used alone or as suffix or prefix, refers to radicals of the general formula —O—AR', wherein —AR' is a heteroaryl.

The term "amine" or "amino" used alone or as a suffix or prefix, refers to radicals of the general formula —NRR', wherein R and R' are independently selected from hydrogen or a hydrocarbon radical.

"Acyl" used alone, as a prefix or suffix, means —C(=O)—R, wherein —R is an optionally substituted hydrocarbyl, hydrogen, amino or alkoxy. Acyl groups include, for example, acetyl, propionyl, benzoyl, phenyl acetyl, carboethoxy, and dimethylcarbamoyl.

Halogen includes fluorine, chlorine, bromine and iodine.

"Halogenated," used as a prefix of a group, means one or more hydrogens on the group are replaced with one or more halogens.

The term "electron-withdrawing group" refers to a chemical group has an electronegativity greater than a methyl group. Electronegativity measures the tendency of a group or atom to attract electrons. Exemplary electron-withdrawing groups are —CH$_2$CF$_3$, —CF$_3$, —F, —Cl, —Br, —NO$_2$, —CN, —OH, —CHO, —C(=O)—R', —OR' and C$_{1-6}$hydrocarbyl substituted by one or more groups selected from —F, —Cl, —Br, —NO$_2$, —CN, —OH, —CHO, —C(=O)—R' and —OR', wherein R' is a C$_{1-3}$alkyl.

"RT" or "rt" means room temperature.

A first ring group being "fused" with a second ring group means the first ring and the second ring share at least two atoms therebetween.

"Link," "linked," or "linking," unless otherwise specified, means covalently linked or bonded.

When a first group, structure, or atom is "directly connected" to a second group, structure or atom, at least one atom of the first group, structure or atom forms a chemical bond with at least one atom of the second group, structure or atom.

"Saturated carbon" means a carbon atom in a structure, molecule or group wherein all the bonds connected to this carbon atom are single bond. In other words, there is no double or triple bonds connected to this carbon atom and this carbon atom generally adopts an sp$^3$ atomic orbital hybridization.

"Unsaturated carbon" means a carbon atom in a structure, molecule or group wherein at least one bond connected to this carbon atom is not a single bond. In other words, there is at least one double or triple bond connected to this carbon atom and this carbon atom generally adopts an sp or Sp$^2$ atomic orbital hybridization.

The term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

DESCRIPTION OF EMBODIMENTS

In one embodiment, the invention provides compounds represented by the formula I, pharmaceutically acceptable salts thereof, diastereomers, enantiomers and mixtures thereof:

(I)

wherein

R$^{F1}$ and R$^{F2}$ are independently C$_{1-10}$ electron-withdrawing groups;

Z is selected from O= and S=;

R$^1$ is selected from C$_{1-10}$alkyl; C$_{1-10}$alkyl substituted by at least one of halogen, cyano, acetoxymethyl and nitro; C$_{2-10}$alkenyl; C$_{2-10}$alkenyl substituted by at least one of halogen, cyano, acetoxymethyl and nitro; C$_{2-10}$alkynyl; C$_{2-10}$alkynyl substituted by at least one of halogen, cyano, acetoxymethyl and nitro; R$^3$R$^4$N—C$_{1-6}$alkyl; R$^3$R$^4$NC(=O)—C$_{1-6}$alkyl; R$^3$O—C$_{1-6}$ alkyl; R$^3$OC(=O)—C$_{1-6}$alkyl; R$^3$C(=O)—C$_{1-6}$alkyl; R$^3$C(=O)NR$^3$—C$_{1-6}$alkyl; R$^4$SO$_2$—C$_{1-6}$alkyl; R$^3$CSO$_2$N(R$^4$)—C$_{1-6}$alkyl; R$^3$R$^4$NC(=O)N(R$^5$)—C$_{1-6}$alkyl; R$^3$R$^4$NSO$_2$N(R$^5$)—C$_{1-6}$alkyl; aryl-C$_{1-6}$alkyl; aryl-C(=O)—C$_{1-6}$alkyl; heterocyclyl-C$_{1-6}$alkyl; heterocyclyl-C(=O)—C$_{1-6}$alkyl; substituted aryl-C$_{1-6}$alkyl; substituted aryl-C(=O)—C$_{1-6}$alkyl; substituted heterocyclyl-C$_{1-6}$alkyl; substituted heterocyclyl-C(=O)—C$_{1-6}$alkyl; and C$_{1-10}$hydrocarbylamino;

R$^3$, R$^4$ and R$^5$ are independently selected from —H, C$_{1-6}$alkyl, C$_{1-6}$alkenyl, C$_{1-6}$alkynyl, and a divalent C$_{1-6}$ group that together with another divalent C$_{1-6}$ group forms a portion of a ring;

X is a C$_{1-10}$ divalent group that separates groups connected thereto by one or two atoms;

Ar is a C$_{4-12}$ divalent aromatic group;

R$^2$ is selected from C$_{1-6}$alkyl, substituted C$_{1-6}$alkyl, C$_{2-6}$alkenyl, substituted C$_{2-6}$alkenyl, C$_{2-6}$alkynyl, substituted C$_{2-6}$alkynyl, C$_{3-6}$cycloalkyl, substituted C$_{1-6}$cycloalkyl, aryl, substituted aryl, and C$_{5-6}$heteroaryl, and substituted C$_{5-6}$heteroaryl; and Y is selected from —CH= and —N=.

In another embodiment, compounds of the present invention may be those of formula I, wherein R$^{F1}$ and R$^{F2}$ are independently C$_{1-6}$alkyl substituted by one or more groups selected from —F, —Cl, —Br, —NO$_2$, —CN, —OH, —CHO, —C(=O)—R' and —OR', wherein R' is a C$_{1-3}$alkyl;

R$^1$ is selected from C$_{1-8}$alkyl; C$_{2-8}$alkenyl; C$_{2-8}$ alkynyl; aryl-C$_{1-6}$alkyl; aryl-C$_{1-6}$alkyl with the aryl substituted by at least one group selected from C$_{1-6}$alkyl, acetoxymethyl, nitro and halogen; R$^8$R$^9$NC$_{1-6}$alkyl; R$^8$OC$_{1-6}$alkyl; cycloalkyl-C$_{1-6}$alkyl; heterocycloalkyl-C$_{1-6}$alkyl; heterocycloalkyl-C$_{1-6}$alkyl with the heterocycloalkyl thereof substituted by at least one group selected from C$_{1-8}$alkyl, acetoxymethyl, nitro and halogen; C$_{1-6}$alkylaryl; C$_{1-6}$alkyl-C(=O)—; C$_{1-8}$aryl-C(=O)—; C$_{4-8}$heteroaryl-C(=O)—; heteroaryl-C$_{1-6}$alkyl; heteroaryl-C$_{1-6}$alkyl with the heteroaryl thereof substituted by at least one group selected from C$_{1-6}$alkyl, acetoxymethyl, nitro and halogen; and R$^N$C$_{1-6}$alkyl;

R$^N$ is an oxidized pyridyl wherein the nitrogen atom of the pyridyl ring is in an oxidized state (N$^+$—O$^-$);

R$^2$ is selected from C$_{1-6}$alkyl, C$_{1-6}$alkyl substituted by at least one fluorine, C$_{1-6}$alkenyl, C$_{1-6}$alkenyl substituted by at least one fluorine, C$_{2-6}$alkynyl, C$_{2-6}$alkynyl substituted by at least one fluorine, C$_{3-6}$cycloalkyl, substituted C$_{1-6}$cycloalkyl, aryl, substituted aryl, and C$_{5-6}$heteroaryl, and substituted C$_{5-6}$heteroaryl;

R$^3$, R$^4$ and R$^5$ are independently selected from —H, C$_{1-6}$alkyl, C$_{1-6}$alkenyl, C$_{1-6}$alkynyl, and a divalent C$_{1-6}$ group that together with another divalent C$_{1-6}$ group forms a portion of a ring; and X is selected from —NR$^6$—, —C(=O)—, —CH$_2$—CH$_2$—, —CH=CH—, —O—, —C(R$^6$)(R$^7$)—, and —S(O)$_q$—, wherein q is 0, 1 or 2, wherein R$^6$ and R$^7$ are independently C$_{1-6}$alkyl, C$_{1-6}$alkenyl, C$_{2-6}$alkynyl, C$_{1-6}$alkoxy, OH, or H.

In a further embodiment, compounds of the present invention may be those of formula I, wherein R$^{F1}$ and R$^{F2}$ are independently selected from —CF$_3$, —CH$_2$CF$_3$, —CH$_2$CHF$_2$, —CHFCF$_3$, —CHFCHF$_2$, —CHFCH$_2$F, —CF$_2$CF$_3$, —CF$_2$CH$_3$, —CF$_2$CH$_2$F, —CF$_2$CHF$_2$, —CCl$_3$, —CH$_2$CCl$_3$, —CH$_2$CHCl$_2$, —CH$_2$CBr$_3$, —CH$_2$CHBr$_2$, —CH$_2$NO$_2$, —CH$_2$CH$_2$NO$_2$, —CH$_2$CN, —CH$_2$CH$_2$CN, and —CH$_2$CH$_2$OCH$_3$;

R$^1$ is selected from C$_{1-8}$alkyl; C$_{2-8}$alenyl; C$_{2-8}$ alkynyl; aryl-C$_{1-6}$alkyl; aryl-C$_{1-6}$alkyl with the aryl substituted by at least one group selected from C$_{1-6}$alkyl, acetoxymethyl, nitro and halogen; R$^8$R$^9$NC$_{1-6}$alkyl; R$^8$OC$_{1-6}$alkyl; cycloalkyl-C$_{1-6}$alkyl; heterocycloalkyl-C$_{1-6}$alkyl; heterocycloalkyl-C$_{1-6}$alkyl with the heterocycloalkyl thereof substituted by at least one group selected from C$_{1-8}$alkyl, acetoxymethyl, nitro and halogen; C$_{1-6}$alkylaryl; C$_{1-6}$alkyl-C(=O)—; C$_{6-8}$aryl-C(=O)—; C$_{4-8}$heteroaryl-C(=O)—; heteroaryl-C$_{1-6}$alkyl; heteroaryl-C$_{1-6}$alkyl with the heteroaryl thereof substituted by at least one group selected from C$_{1-6}$alkyl, acetoxymethyl, nitro and halogen; and R$^N$C$_{1-6}$alkyl;

R$^N$ is an oxidized pyridyl wherein the nitrogen atom of the pyridyl ring is in an oxidized state (N$^+$—O$^-$);

Z is O=;

R$^2$ is selected from —CH$_3$, —CH$_2$CH$_3$, —CH(CH$_3$)$_2$, C$_{3-6}$cycloalkyl, —CH$_2$CF$_3$, —CHF$_2$, —CF$_3$ and aryl;

Ar is selected from an arylene; an heteroarylene; an arylene substituted by at least one group selected from C$_{1-6}$alkyl, halogen, trifluoromethyl, cyano, nitro, hydroxy and C$_{1-6}$alkoxy, and an heteroarylene substituted by at least one group selected from C$_{1-6}$alkyl, halogen, trifluoromethyl, cyano, nitro, hydroxy and C$_{1-6}$alkoxy, even more particularly, the arylene is para-arylene; and the heteroarylene is selected from the group consisting of six-membered ring para-heteroarylene and five-membered ring meta-heteroarylene; and R$^8$ and R$^9$ are independently selected from the group consisting of —H and C$_{1-6}$alkyl.

In an even further embodiment, compounds of the present invention may be those of formula I, wherein R$^{F1}$ and R$^{F2}$ are independently C$_{1-6}$ groups that comprise at least 30% fluorine by weight;

Z is O=;

R$^1$ is selected from ethyl, propyl, alkyl, isopentyl, benzyl, dimethylaminoethyl, 4-pyridylmethyl, 2-pyridylmethyl, 1-pyrrolylethyl, cyclopropylmethyl, cyclobutylmethyl, cyclopentylmethyl, cyclohexylmethyl, 2-pyrrolidylmethyl, 3-pyrrolidylmethyl, N-methyl-2-pyrrolidylmethyl, N-methyl-3-pyrrolidylmethyl, 2-piperidylmethyl, 3-piperidylmethyl, 4-piperidylmethyl, N-methyl-2-piperidylmethyl, N-methyl-3-piperidylmethyl, N-methyl-4-piperidylmethyl, 3-thienylmethyl, 2-tetrahydrofuranylmethyl, 3-tetrahydrofuranylmethyl, 2-tetrahydropyranylmethyl, 3-tetrahydropyranylmethyl, 4-tetrahydropyranylmethyl, (2-nitrothiophene-5-yl)methyl, (1-methyl-1H-imidazole-2-yl)methyl, (5-(acetoxymethyl)-2-furanyl)methyl, (2,3-dihydro-1H-isoindole-1-yl)methyl, and 5-(2-methylthiazolyl);

R$^2$ is selected from —CH$_3$, —CH$_2$CH$_3$, —CH(CH$_3$)$_2$, —CH$_2$CF$_3$, CF$_3$, cyclopropyl, cyclobutyl, cyclopentyl, cyclohexyl and phenyl;

X is selected from —CH$_2$— and —CH(CH$_3$)—; and

Ar is selected from a para-arylene; a para-arylene substituted with C$_{1-6}$alkyl, halogen, trifluoromethyl, cyano, nitro, hydroxy and C$_{1-6}$alkoxy; a six-membered ring para-heteroarylene; and a six-membered ring para-heteroarylene substituted with a group selected from C$_{1-6}$alkyl, halogen, trifluoromethyl, cyano, nitro, hydroxy and C$_{1-6}$alkoxy.

In an even further embodiment, R$^{F1}$ and R$^{F2}$ are —CH$_2$CF$_3$; R$^2$ is —CH$_2$CH$_3$; and Ar is selected from the group consisting of para-phenylene and para-pyridylene.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkylamine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

The compounds of the invention may have activity as pharmaceuticals, in particular as modulators or ligands such as agonists, partial agonists, inverse agonist or antagonists of $CB_2$ receptors. In one embodiment, the compounds of the invention may exhibit selective activity as agonists at $CB_2$ receptors, and are useful in the relief of pain, particularly chronic pain, e.g., chronic inflammatory pain, neuropathic pain, back pain, cancer pain and visceral pain. Compounds of the present invention may also be useful in treating acute pain. Additionally, compounds of the present invention may be useful in other disease states in which degeneration or dysfunction of $CB_2$ receptors is present or implicated.

Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

The compounds of the present invention may be useful in therapy, especially for the therapy of various pain conditions including, but not limited to: acute pain, chronic pain, neuropathic pain, back pain, cancer pain, and visceral pain.

The compounds of the present invention may also be used in treating pain, cancer, multiple sclerosis, Parkinson's disease, transplant rejection, Huntington's chorea and/or Alzheimer's disease.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skill in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, acute pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

In one embodiment, the compounds of the invention are found to be active towards $CB_2$ receptors in warm-blooded animals, e.g., human. Particularly the compounds of the invention are found to be effective $CB_2$ receptor agonists. In vitro assays, infra, demonstrate these activities. In these in vitro assays, a compound is tested for their activity toward $CB_2$ receptors and dissociation constant (Ki) is obtained to determine the selective activity for a particular compound towards $CB_2$ receptors by measuring $IC_{50}$ of the compound. In the current context, $IC_{50}$ generally refers to the concentration of the compound at which 50% displacement of a standard radioactive $CB_2$ receptor ligand has been observed. Generally, a lower Ki for a particular compound towards $CB_2$ receptors means that the particular compound is a stronger ligand towards the $CB_2$ receptors. As a result, compounds with relatively low Ki towards $CB_2$ receptors are relatively strong $CB_2$ receptor ligands or potent $CB_2$ receptor agonists.

The activities of the compound towards $CB_1$ receptors are also measured in a similar assay. It is known that even though $CB_1$ receptor agonists are also effective in relieving or managing pains, their use is often associated with undesired CNS side-effects, e.g., psychoactive side effects and abuse potential. In one embodiment, we surprisingly find the particular compounds of the present invention tend to bind weakly to $CB_1$ receptors, have relatively high Ki's towards particular $CB_1$ receptors and thus low binding affinity toward $CB_1$ receptors. As a result, the compounds may show no or less side effects in treating pain in comparison with conventional cannabinoids.

$CB_2$ receptors are generally expressed in peripheral tissues, particularly in the immuno-competent and inflammatory cells, which are believed to have therapeutic effects related to immunomodulation, inflammation and bronchial-constriction. The $CB_2$ receptor selective ligands such as $CB_2$ receptor agonists may have therapeutic utility in controlling diseases associated with these conditions.

It is substantially established that $CB_2$ receptor ligands (e.g. agonists) are generally effective in treating or managing pain in warm-blooded animals with little side effects such as addiction and the $CB_2$ receptor ligands may have similar effects on humans. For example, $CB_2$ receptors have been found to be expressed in peritoneal mast cells which play a crucial role in amplifying the key nerve growth factor (NGF) which may induce inflammatory hyperalgesia. $CB_2$ receptors have also been shown to be involved in the attenuation of nitric oxide production from macrophages upon treatment of LPS.

In addition, in vivo pain models have shown that $CB_2$ receptor agonists may induce analgesia. In particular, it has been found that the expression of the $CB_2$ receptors is induced under conditions of immune cell activation and that a $CB_2$ agonist elicits anti-inflammatory and peripheral analgesic activity. Moreover, it has been shown that $CB_2$ activation inhibits mechanical hyperalgesia associated with nerve injury. Further, it has been demonstrated that peripheral $CB_2$ receptors may mediate antinociception in the rat. Consequentially, in one embodiment, the compounds that show a lower Ki in the in vitro assays disclosed in the invention may be suitable to be used in therapies such as pain relief or pain management.

$CB_2$ receptor selective ligands such as $CB_2$ receptor agonists (sometimes also called $CB_2$ selective cannabinoids) have been shown to induce apoptosis in glioma cells, in both in vitro and in vivo settings. Further evidence has supported the antiproliferative effects of $CB_2$ receptor agonists on breast and prostate cancer cells. $CB_2$ receptor agonists can also induce tumor suppression in a rat model in which rat glioma C6 cells are inoculated intracerebrally in the rats. Both clinical and non-clinical studies also show that $CB_2$ receptor ligands may also have a positive effect on multiple sclerosis.

$CB_2$ receptor agonists may also be used in other therapies related directly or indirectly to immunomodulation such as treating asthma, bronchitis, chronic obstructive pulmonary disease (COPD), reversible airway obstruction, adult respiratory distress syndrome, psoriasis, rheumatoid arthritis, and allergy. $CB_2$ receptor agonists may also be effective in treating Parkinson's disease, Huntington's chorea and Alzheimer's disease, and Crohn's disease. $CB_2$ receptor agonists may also be useful in transplant rejection therapy.

Therefore, in another aspect, the compounds of the invention may be useful and effective in treating LPS, pain, multiple sclerosis, asthma, bronchitis, chronic obstructive pulmonary disease (COPD), reversible airway obstruction, adult respiratory distress syndrome, psoriasis, rheumatoid arthritis, allergy, Parkinson's disease, Huntington's chorea and Alzheimer's disease, Crohn's disease, and transplant rejection.

In a further aspect, the present invention provides a method of preparing a compound of formula I.

In one embodiment, the method of preparing the compound of the invention includes the step of reacting a compound represented by formula II with $R^2OArXC(=O)A$:

(II)

wherein $R^{F1}$ and $R^{F2}$ are independently electron-withdrawing groups;

Z is selected from O= and S=;

$R^1$ is a $C_{1-11}$ group;

X is a divalent group that separates groups connected thereto by one or two atoms;

A is selected from —OH, —Cl, —Br, and —I;

Ar is selected from a divalent aromatic group;

$R^2$ is a $C_{1-6}$ group; and

Y is selected from —CH= and —N=.

In another embodiment, $R^{F1}$, $R^{F2}$, $R^1$, $R^2$, Z, X, Ar, and Y are the same as those defined in the context of defining formula I.

In a further embodiment, the reaction conditions for the above reaction step may be as follows:

Process a) A compound of formula II and $R^2$OArX(C=O)A may be reacted together in a suitable solvent (e.g. 1,2-dichloroethane) in the presence of a reducing agent (e.g., zinc) followed by treatment with an acid (e.g., HCl) with heating (e.g., at 70-100° C.) to form a compound of formula I, wherein A is —Cl, —Br or —I.

Process b) A compound of formula II and $R^2$OArX(C=O)OH may be reacted together in a suitable polar solvent (e.g., dimethylformamide (DMF)) in the presence of O-(7-azabenzotriazol-1-yl)-N,N,N',N'-tetramethyl uronium hexafluorophosphate (HATU) and a base such as diisopropylethylamine (DIPEA) followed by treatment with an acid (e.g. HCl) with heating (e.g., at 70-100° C.) to form a compound of formula I.

In another embodiment, the method of preparing the compound of the invention includes the step of reacting a compound represented by formula III with formaldehyde:

(III)

wherein r and s are selected from 0, 1 and 2;

$R^{10}$ is selected from $C_{1-6}$alkylene, —O—, and —$NR^{11}$—, wherein $R^{11}$ is a $C_{1-6}$alkyl;

$R^{F1}$ and $R^{F2}$ are independently electron-withdrawing groups;

X is a divalent group that separates groups connected thereto by one or two atoms;

Ar is a divalent aromatic group;

A is selected from —OH, —Cl, —Br, and —I.

$R^2$ is a $C_{1-6}$ group; and

Y is selected from —CH= and —N=.

In a further embodiment, $R^{F1}$, $R^{F2}$, $R^2$, X, Ar, and Y are the same as those defined in the context of defining formula I.

In an even further embodiment, the reaction conditions for the above reacting step may be as follows:

A compound of formula III and formaldehyde may be reacted together in a suitable solvent (e.g. methanol, or tetrahydrofuran (THF)) in the presence of a reducing or hydrogenation agent (e.g., NaCNBH$_3$, NaBH(OAc)$_3$), optionally further in the presence of an acid such as acetic acid, to form a compound of formula I.

In an even further embodiment, the compounds of the present invention can be prepared according to the synthetic routes as depicted in Schemes 1 and 2.

Scheme 1

-continued

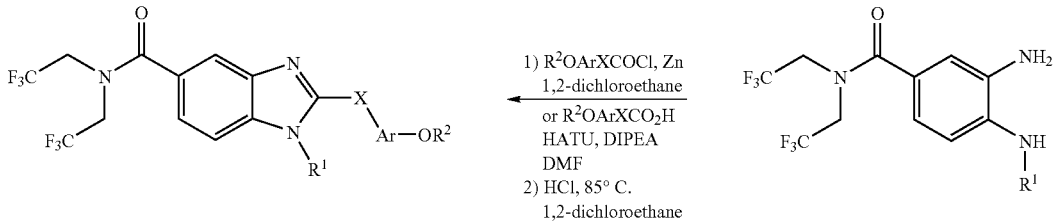

R¹, R², Ar, X are the same as defined above.

Scheme 2

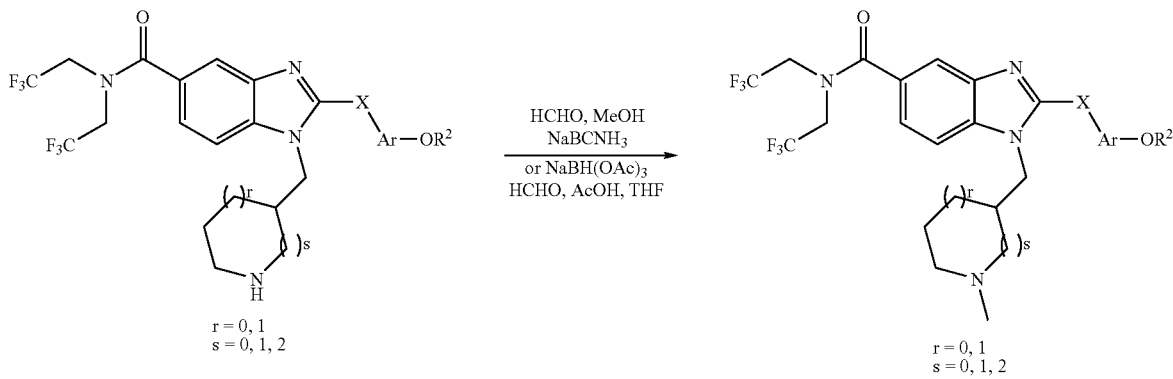

Ar, X and R² are the same as defined above.

EXAMPLES

The invention will further be described in more detail by the following Examples which describe methods whereby compounds of the present invention may be prepared, purified, analyzed and biologically tested, and which are not to be construed as limiting the invention.

Example 1

Biological Evaluation hCB$_1$ and hCB$_2$ Receptor Binding

Human CB$_1$ receptor from Receptor Biology (hCB1) or human CB$_2$ receptor from BioSignal (hCB2) membranes are thawed at 37° C., passed 3 times through a 25-gauge blunt-end needle, diluted in the cannabinoid binding buffer (50 mM Tris, 2.5 mM EDTA, 5 mM MgCl$_2$, and 0.5 mg/mL BSA fatty acid free, pH 7.4) and aliquots containing the appropriate amount of protein are distributed in 96-well plates. The IC$_{50}$ of the compounds of the invention at hCB$_1$ and hCB$_2$ are evaluated from 10-point dose-response curves done with $^3$H-CP55,940 at 20000 to 25000 dpm per well (0.17-0.21 nM) in a final volume of 300 µl. The total and non-specific binding are determined in the absence and presence of 0.2 µM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM MgCl$_2$, 0.5 mg BSA pH 7.0). The filters are dried for 1 hour at 55° C. The radioactivity (cpm) is counted in a TopCount (Packard) after adding 65 µl/well of MS-20 scintillation liquid.

hCB$_1$ and hCB$_2$ GTPγS Binding

Human CB$_1$ receptor from Receptor Biology (hCB1) or human CB$_2$ receptor membranes (BioSignal) are thawed at 37° C., passed 3 times through a 25-gauge blunt-end needle and diluted in the GTPγS binding buffer (50 mM Hepes, 20 mM NaOH, 100 mM NaCl, 1 mM EDTA, 5 mM MgCl$_2$, pH 7.4, 0.1% BSA). The EC$_{50}$ and E$_{max}$ of the compounds of the invention are evaluated from 10-point dose-response curves done in 300 µl with the appropriate amount of membrane protein and 100000-130000 dpm of GTPg$^{35}$S per well (0.11-0.14 nM). The basal and maximal stimulated binding is determined in absence and presence of 1 µM (hCB$_2$) or 10 µM (hCB$_1$) Win 55,212-2 respectively. The membranes are pre-incubated for 5 minutes with 56.25 )M (hCB$_2$) or 112.5 µM (hCB$_1$) GDP prior to distribution in plates (15 µM (hCB$_2$) or 30 µM (hCB$_1$) GDP final). The plates are vortexed and incubated for 60 minutes at room temperature, filtered on Unifilters GF/B (presoaked in water) with the Tomtec or Packard harvester using 3 ml of wash buffer (50 mM Tris, 5 mM MgCl$_2$, 50 mM NaCl, pH 7.0). The filters are dried for 1 hour at 55° C. The radioactivity (cpm) is counted in a TopCount (Packard) after adding 65 µl/well of MS-20 scintillation liquid. Antagonist reversal studies are done in the same way except that (a) an agonist dose-response curve is done in the presence of a constant concentration of antagonist, or (b) an antagonist dose-response curve is done in the presence of a constant concentration of agonist.

Based on the above assays, the dissociation constant (Ki) for a particular compound of the invention towards a particular receptor is determined using the following equation:

$$Ki=IC_{50}/(1+[rad]/Kd),$$

Wherein IC$_{50}$ is the concentration of the compound of the invention at which 50% displacement has been observed;

[rad] is a standard or reference radioactive ligand concentration at that moment; and Kd is the dissociation constant of the radioactive ligand towards the particular receptor.

Biological data for certain compounds of the invention are listed in Table 1 below.

TABLE 1

Biological data

| Compound No. | Structure | hCB1 Ki (nM) | hCB2 Ki (nM) |
|---|---|---|---|
| 1 | | 2799.9 | 3.1 |
| 2 | | 5084.4 | 5.6 |
| 3 | | 84.8 | 0.8 |
| 4 | | 4694.1 | 13.9 |

TABLE 1-continued

| Compound No. | Structure | hCB1 Ki (nM) | hCB2 Ki (nM) |
|---|---|---|---|
| 5 | | 5388.1 | 44.1 |
| 6 | | 5531.5 | 42.7 |
| 7 | | 5531.5 | 53.1 |
| 8 | | 5350.0 | 16.7 |

TABLE 1-continued
Biological data
| Compound No. | | hCB1 Ki (nM) | hCB2 Ki (nM) |
|---|---|---|---|
| 9 | 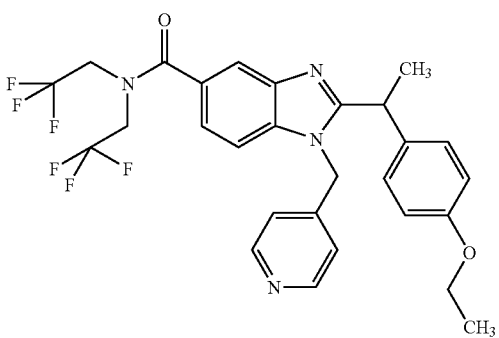 | 5568.0 | 164.9 |
| 10 | 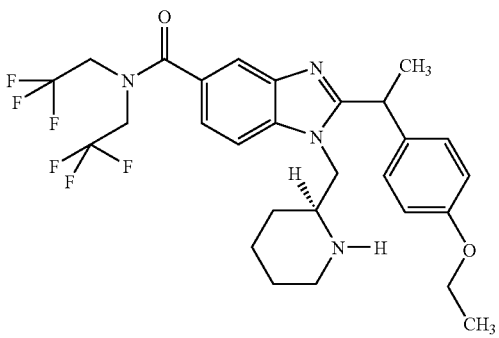 | 3502.4 | 28.2 |
| 11 | 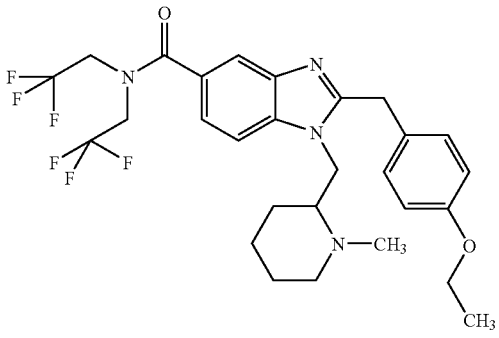 | 3234.4 | 12.0 |
| 12 | 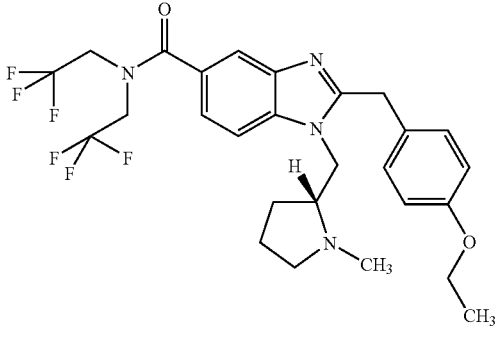 | 5715.4 | 12.5 |

TABLE 1-continued

Biological data

| Compound No. | Structure | | hCB1 Ki (nM) | hCB2 Ki (nM) |
|---|---|---|---|---|
| 13 | | | 565.4 | 5.4 |
| 14 | | Chiral | 5749.8 | 14.8 |
| 15 | | Chiral | 5749.8 | 9.6 |
| 16 | | | 1414.0 | 3.3 |

TABLE 1-continued

Biological data

| Compound No. | | hCB1 Ki (nM) | hCB2 Ki (nM) |
|---|---|---|---|
| 17 | Chiral | 2964.0 | 19.3 |
| 18 | Chiral | 5583.4 | 179.8 |
| 19 | Chiral | 1315.5 | 7.3 |
| 20 | | 2729.2 | 11.2 |

TABLE 1-continued

Biological data

| Compound No. | Structure | | hCB1 Ki (nM) | hCB2 Ki (nM) |
|---|---|---|---|---|
| 21 | (benzimidazole with N,N-bis(2,2,2-trifluoroethyl)carboxamide, N1-isopentyl, 2-(5-ethoxypyridin-2-yl)methyl) | | 5433.4 | 15.4 |
| 22 | (benzimidazole with N,N-bis(2,2,2-trifluoroethyl)carboxamide, N1-[(1-methylpiperidin-2-yl)methyl], 2-(5-ethoxypyridin-2-yl)methyl) | Chiral | 5523.1 | 23.1 |
| 23 | (benzimidazole with N,N-bis(2,2,2-trifluoroethyl)carboxamide, N1-[(4-methylmorpholin-3-yl)methyl], 2-(4-ethoxybenzyl)) | | 5572.3 | 55.8 |
| 24 | (benzimidazole with N,N-bis(2,2,2-trifluoroethyl)carboxamide, N1-[(1-methylpiperidin-2-yl)methyl], 2-(4-ethoxybenzyl)) | Chiral | 5746.9 | 138.4 |

TABLE 1-continued
Biological data
| Compound No. | | hCB1 Ki (nM) | hCB2 Ki (nM) |
|---|---|---|---|
| 25 | 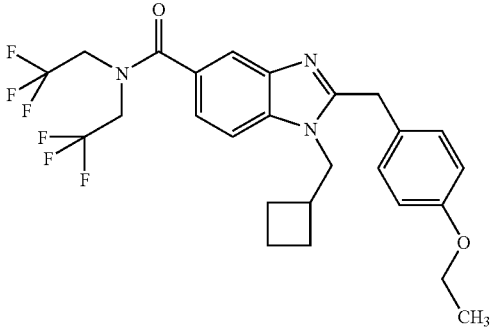 | 1555.4 | 2.0 |
| 26 | 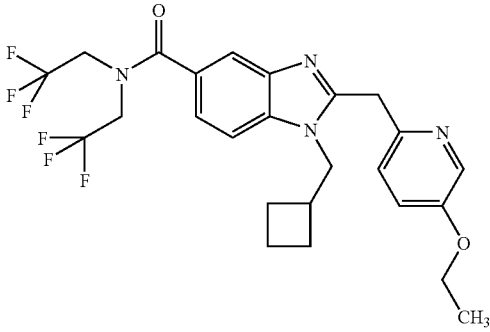 | 5528.7 | 6.6 |
| 27 | 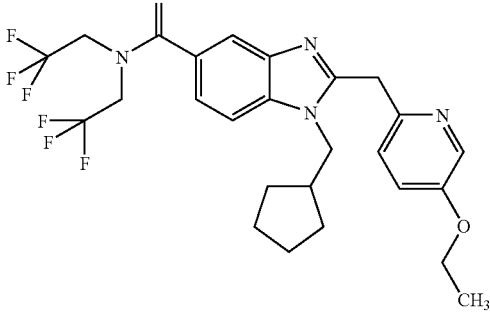 | 1356.8 | 3.2 |
| 28 | 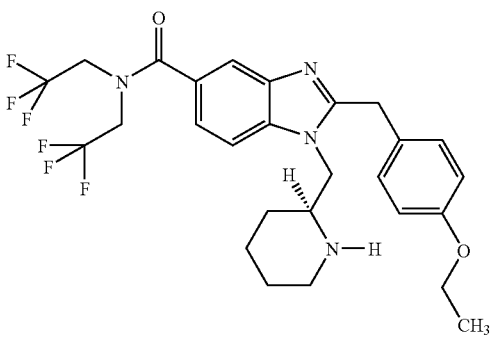 Chiral | 5538.6 | 40.5 |

TABLE 1-continued

Biological data

| Compound No. | Structure | | hCB1 Ki (nM) | hCB2 Ki (nM) |
|---|---|---|---|---|
| 29 | | | 5814.9 | 68.7 |
| 30 | | | 454.9 | 3.1 |
| 31 | | Chiral | 826.4 | 13.5 |
| 32 | | | 142.0 | 2.7 |

TABLE 1-continued

Biological data

| Compound No. | | hCB1 Ki (nM) | hCB2 Ki (nM) |
| --- | --- | --- | --- |
| 33 | | 5178.8 | 446.6 |
| 34 | Chiral | 5378.2 | 78.2 |
| 35 | | 5572.3 | 1585.1 |
| 36 | | 5751.1 | 14.0 |

Example 2      Synthesis of Intermediates 1-39

Intermediate 1

4-Fluoro-3-nitro-N,N-bis(2,2,2-trifluoroethyl)benzamide

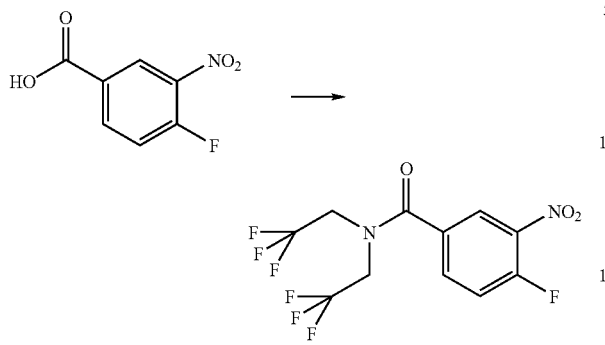

4-Fluoro-3-nitrobenzoic acid (2.50 g, 13.5 mmol) was refluxed in a 2:1 mixture of CH$_2$Cl$_2$/SOCl$_2$ (150 mL) for 5 h. The solvent was concentrated and the residue was dissolved in CH$_2$Cl$_2$ (50 mL). Another CH$_2$Cl$_2$ solution (50 mL) of diisopropylethylamine (DIPEA) (3.50 mL, 20.3 mmol) and bis(2,2,2-trifluoroethyl)amine (4.90 g, 27.0 mmoL) was then added dropwise to the cold stirring solution (0° C.) of the acid chloride. The solution was stirred at RT overnight. The solution was then washed with 5% KHSO$_4$ solution, saturated NaHCO$_3$ solution, and brine and dried over anhydrous MgSO$_4$. The product was purified by flash chromatography on silica gel using 3:1/HEX:EtOAc. Yield: 3.08 g (66%); $^1$H NMR (CDCl$_3$) 4.17 (brs, 4H), 7.40 (t, J=8.59 Hz, 1H), 7.66 (m, 2H), 8.10 (d, J=6.84 Hz, 1H).

Intermediate 2

4-[(3-Methylbutyl)amino]-3-nitro-N,N-bis(2,2,2-trifluoroethyl)-benzamide

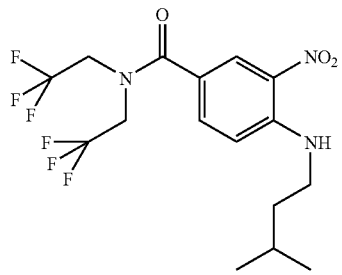

4-Fluoro-3-nitro-N,N-bis(2,2,2-trifluoroethyl)benzamide (170 mg, 0.488 mmol) and isoamylamine (0.068 mL, 0.586 mmol) were stirred in 3 mL of EtOH containing Et$_3$N (0.136 mL, 0.976 mmol) at 80° C. for 3 h. The solvent was concentrated. The residue was dissolved in EtOAc and washed with saturated NaHCO$_3$, brine and dried over anhydrous Na$_2$SO$_4$. The product was purified by flash chromatography on silica gel using 3:1/hexanes:EtOAc as eluent affording intermediate 2 as a yellow oil. Yield: 203 mg (99%); $^1$H NMR (CDCl$_3$) 1.00 (d, J=6.64 Hz, 6H), 1.67 (m, 2H), 1.79 (m, 1H), 3.36 (m, 2H), 4.25 (q, J=8.59 Hz, 4H), 6.95 (d, J=8.98 Hz, 1H), 7.57 (d, J=8.98 Hz, 1H), 8.30 (m, 2H); MS (ESI) 416.22 (MH+).

Intermediate 3

4-[(Cyclopropylmethyl)amino]-3-nitro-N,N-bis(2,2,2-trifluoroethyl)-benzamide

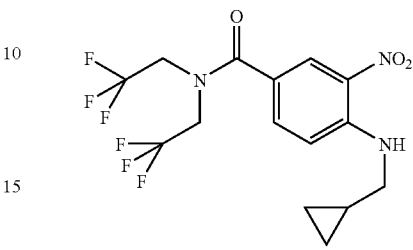

Following the general procedure for Intermediate 2 using 4-fluoro-3-nitro-N,N-bis(2,2,2-trifluoroethyl)benzamide (100 mg, 0.287 mmol) and cyclopropylmethyl amine (0.030 mL, 0.344 mmol) in 3 mL of EtOH containing Et$_3$N (0.080 mL, 0.574 mmol). The product was purified by flash chromatography on silica gel using 4:1/hexanes:EtOAc as eluent. Yield: 91 mg (80%); $^1$H NMR (CDCl$_3$) 0.35 (m, 2H), 0.70 (m, 2H), 1.21 (m, 1H), 3.21 (m, 2H), 4.25 (q, J=8.59 Hz, 4H), 6.91 (d, J=8.98 Hz, 1H), 7.54 (d, J=8.79 Hz, 1H), 8.30 (s, 1H), 8.35 (s, 1H); MS (ESI) 400.19 (MH+).

Intermediate 4

4-[(Cyclohexylmethyl)amino]-3-nitro-N,N-bis(2,2,2-trifluoroethyl)-benzamide

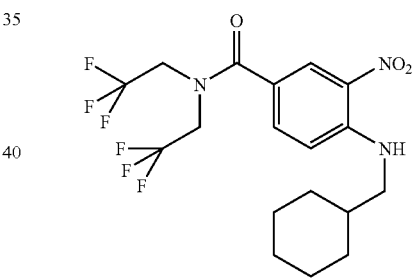

Following the general procedure for Intermediate 2 using 4-fluoro-3-nitro-N,N-bis(2,2,2-trifluoroethyl)benzamide (100 mg, 0.287 mmol) and cyclohexylmethyl amine (0.041 mL, 0.315 mmol) in 3 mL of EtOH containing Et$_3$N (0.080 mL, 0.574 mmol). The product was purified by flash chromatography on silica gel using 4:1/hexanes:EtOAc as eluent. Yield: 107 mg (85%); $^1$H NMR (CDCl$_3$) 1.05 (m, 2H), 1.24 (m, 4H), 1.69 (m, 2H), 1.75 (m, 2H), 1.83 (m, 1H), 3.17 (t, J=6.64 Hz, 2H), 4.23 (q, J=8.53 Hz, 4H), 6.91 (d, J=8.98 Hz, 1H), 7.51 (d, J=8.89 Hz, 1H), 8.28 (s, 1H), 8.39 (s, 1H); MS (ESI) 442.29 (MH+).

Intermediate 5

4-[(2-Furanylmethyl)amino]-3-nitro-N,N-bis(2,2,2-trifluoroethyl)-benzamide

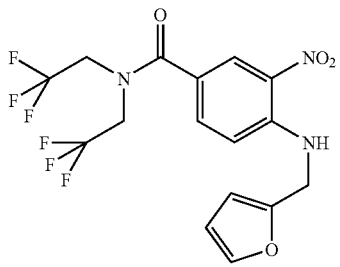

Following the general procedure for Intermediate 2 using 4-fluoro-3-nitro-N,N-bis(2,2,2-trifluoroethyl)benzamide (100 mg, 0.287 mmol) and furfurylamine (0.028 mL, 0.315 mmol) in 3 mL of EtOH containing Et$_3$N (0.080 mL, 0.574 mmol). The product was purified by flash chromatography on silica gel using 4:1/hexanes:EtOAc as eluent. Yield: 115 mg (94%); $^1$H NMR (CDCl$_3$) 4.23 (q, J=8.40 Hz, 4H), 4.56 (d, J=5.66 Hz, 2H), 6.31 (d, J=3.12 Hz, 1H), 6.35 (m, 1H), 7.04 (d, J=8.98 Hz, 1H), 7.39 (s, 1H), 7.53 (d, J=8.89 Hz, 1H), 8.28 (s, 1H), 8.55 (s, 1H); MS (ESI) 426.21 (MH+).

Intermediate 6

2-[[[4-[[Bis(2,2,2-trifluoroethyl)amino]carbonyl]-2-nitrophenyl]amino]methyl]-(2S)-1-pyrrolidinecarboxylic acid-1,1-dimethylethyl ester

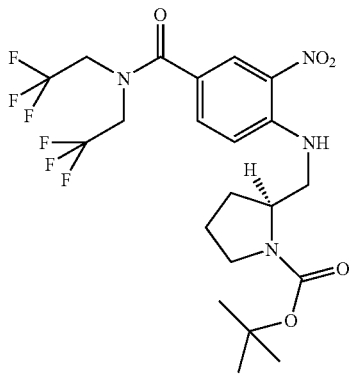

Following the general procedure for Intermediate 2 using 4-fluoro-3-nitro-N,N-bis(2,2,2-trifluoroethyl)benzamide (130 mg, 0.373 mmol) and (S)-2-aminomethyl-1-Boc-pyrrolidine (82 mg, 0.410 mmol) in 3 mL of EtOH containing Et$_3$N (0.080 mL, 0.559 mmol). The product was purified by flash chromatography on silica gel using 3:1/hexanes:EtOAc as eluent. Yield: 165 mg (84%); $^1$H NMR (CDCl$_3$) 1.47 (brs, 9H), 1.83 (m, 1H), 1.90 (m, 2H), 2.03 (m, 1H), 3.31 (m, 1H), 3.37 (m, 2H), 3.62 (m, 1H), 4.09 (m, 2H), 4.24 (m, 6H), 7.26 (m, 1H), 7.50 (m, 1H), 8.27 (s, 1H), 8.55 (brs, 1H); MS (ESI) 529.38 (MH+).

Intermediate 7

2-[[[4-[[Bis(2,2,2-trifluoroethyl)amino]carbonyl]-2-nitrophenyl]amino]methyl]-(2R)-1-pyrrolidinecarboxylic acid-1,1-dimethylethyl ester

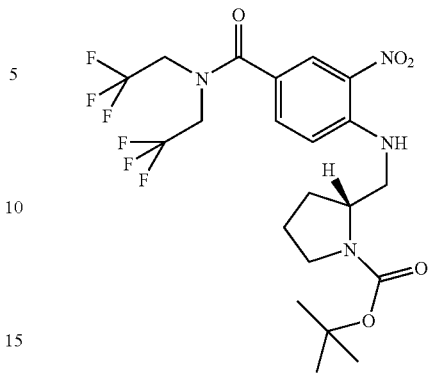

Following the general procedure for Intermediate 2 using 4-fluoro-3-nitro-N,N-bis(2,2,2-trifluoroethyl)benzamide (157 mg, 0.450 mmol) and (R)-2-aminomethyl-1-Boc-pyrrolidine (100 mg, 0.495 mmol) in 3 mL of EtOH containing Et$_3$N (0.095 mL, 0.559 mmol). The product was purified by flash chromatography on silica gel using 3:1/hexanes:EtOAc as eluent. Yield: 232 mg (98%); $^1$H NMR (CDCl$_3$) 1.47 (brs, 9H), 1.83 (m, 1H), 1.90 (m, 2H), 2.03 (m, 1H), 3.31 (m, 1H), 3.37 (m, 2H), 3.62 (m, 1H), 4.09 (m, 2H), 4.24 (m, 6H), 7.26 (m, 1H), 7.50 (m, 1H), 8.27 (s, 1H), 8.55 (brs, 1H); MS (ESI) 529.38 (MH+).

Intermediate 8

3-Nitro-4-[(4-pyridinylmethyl)amino]-N,N-bis(2,2,2-trifluoroethyl)-benzamide

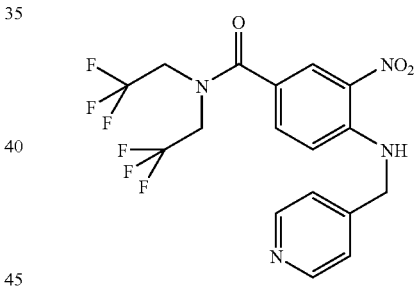

4-Fluoro-3-nitro-N,N-bis(2,2,2-trifluoroethyl)benzamide (120 mg, 0.345 mmol) and 4-(aminomethyl)pyridine (0.070 mL, 0.380 mmoL) were stirred in 3 mL of CH$_3$CN. The solvent was concentrated. The residue was dissolved in EtOAc and washed with saturated NaHCO$_3$, brine and dried over anhydrous Na$_2$SO$_4$. The product was purified by flash chromatography on silica gel using EtOAc as eluent affording the title compound as yellow oil. Yield: 145 mg (79%); $^1$H NMR (CDCl$_3$) 4.19 (q, J=8.59 Hz, 4H), 4.71 (d, J=6.25 Hz, 2H), 6.69 (d, J=8.79 Hz, 1H), 7.45 (m, 3H), 8.32 (s, 1H), 8.65 (d, J=6.25 Hz, 2H), 8.73 (m, 1H); MS (ESI) 437.24 (MH+).

Intermediate 9

3-Nitro-4-[[(tetrahydro-2H-pyran-4-yl)methyl]amino]-N,N-bis(2,2,2-trifluoroethyl)benzamide

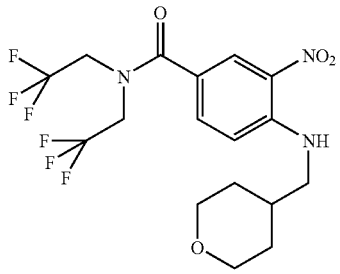

Following the general procedure for Intermediate 2 using 4-fluoro-3-nitro-N,N-bis(2,2,2-trifluoroethyl)benzamide (75 mg, 0.215 mmol) and 4-aminomethyltetrahydropyran (27 mg, 0.236 mmol) in 3 mL of EtOH containing Et₃N (0.045 mL, 0.323 mmol). The product was purified by flash chromatography on silica gel using 2:1/hexanes:EtOAc as eluent. Yield: 87 mg (91%); ¹H NMR (CDCl₃) 1.47 (m, 2H), 1.75 (m, 2H), 1.98 (m, 1H), 3.27 (t, J=5.47 Hz, 2H), 3.43 (m, 2H), 4.03 (m, 2H), 4.24 (q, J=8.33 Hz, 6H), 6.93 (d, J=8.98 Hz, 1H), 7.54 (d, J=8.98 Hz, 1H), 8.30 (s, 1H), 8.40 (brs, 1H); MS (ESI) 444.31 (MH+).

Intermediate 10

3-Nitro-4-[[[(2R)-tetrahydro-2-furanyl]methyl]amino]-N,N-bis(2,2,2-trifluoroethyl)-benzamide

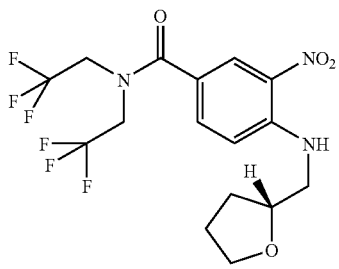

Following the general procedure for Intermediate 2 using 4-fluoro-3-nitro-N,N-bis(2,2,2-trifluoroethyl)benzamide (78 mg, 0.224 mmol) and R-(−)-tetrahydrofurfurylamine (0.025 mL, 0.246 mmol) in 3 mL of EtOH containing Et₃N (0.047 mL, 0.336 mmol). The product was purified by flash chromatography on silica gel using 2:1/hexanes:EtOAc as eluent. Yield: 96 mg (95%); ¹H NMR (CDCl₃) 1.72 (m, 1H), 1.99 (m, 2H), 2.13 (m, 1H), 3.99 (m, 1H), 3.53 (m, 1H), 3.85 (m, 1H), 3.97 (m, 1H), 4.25 (m, 5H), 6.99 (d, J=8.98 Hz, 1H), 7.53 (d, J=8.98 Hz, 1H), 8.30 (s, 1H), 8.51 (brs, 1H); MS (ESI) 430.31 (MH+).

Intermediate 11

3-Nitro-4-[[[(2S)-tetrahydro-2-furanyl]methyl]amino]-N,N-bis(2,2,2-trifluoroethyl)-benzamide

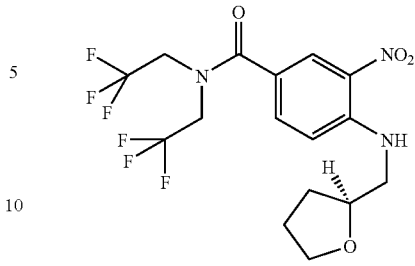

Following the general procedure for Intermediate 2 using 4-fluoro-3-nitro-N,N-bis(2,2,2-trifluoroethyl)benzamide (78 mg, 0.224 mmol) and S-(+)-tetrahydrofurfurylamine (0.025 mL, 0.246 mmol) in 3 mL of EtOH containing Et₃N (0.047 mL, 0.336 mmol). The product was purified by flash chromatography on silica gel using 1:1/hexanes:EtOAc as eluent. Yield: 95 mg (95%); ¹H NMR (CDCl₃) 1.72 (m, 1H), 1.99 (m, 2H), 2.13 (m, 1H), 3.99 (m, 1H), 3.53 (m, 1H), 3.85 (m, 1H), 3.97 (m, 1H), 4.25 (m, 5H), 6.99 (d, J=8.98 Hz, 1H), 7.53 (d, J=8.98 Hz, 1H), 8.30 (s, 1H), 8.51 (brs, 1H); MS (ESI) 430.28 (MH+).

Intermediate 12

3-Nitro-4-[[[(tetrahydro-2H-pyran-2-yl)methyl]amino]-N,N-bis(2,2,2-trifluoroethyl)-benzamide

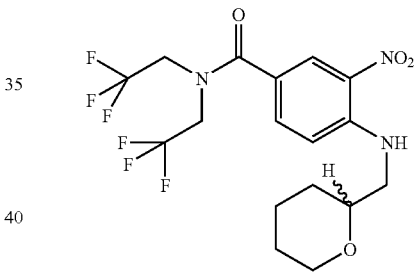

Following the general procedure for Intermediate 2 using 4-fluoro-3-nitro-N,N-bis(2,2,2-trifluoroethyl)benzamide (83 mg, 0.238 mmol) and R/S-2-aminomethyl-tetrahydropyran hydrochloride (40 mg, 0.262 mmol) in 3 mL of EtOH containing Et₃N (0.070 mL, 0.476 mmol). The product was purified by flash chromatography on silica gel using 2:1/hexanes:EtOAc as eluent. Yield: 100 mg (95%); ¹H NMR (CDCl₃) 1.48 (m, 1H), 1.58 (m, 3H), 1.68 (m, 1H), 1.95 (m, 1H), 3.35 (m, 1H), 3.41 (m, 1H), 3.52 (m, 1H), 3.64 (m, 1H), 4.07 (m, 1H), 4.26 (m, 4H), 6.96 (d, J=8.98 Hz, 1H), 7.54 (d, J=8.98 Hz, 1H), 8.31 (s, 1H), 8.55 (brs, 1H); MS (ESI) 530.21 (MH+).

Intermediate 13

2-[[[4-[[Bis(2,2,2-trifluoroethyl)amino]carbonyl]-2-nitrophenyl]amino]methyl]-(2R)-1-piperidinecarboxylic acid-1,1-dimethylethyl ester

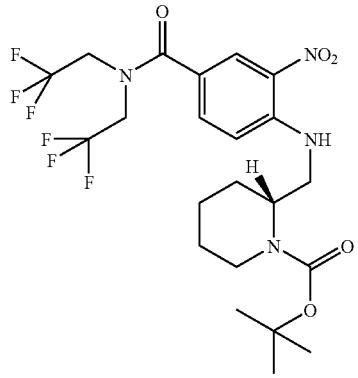

Following the general procedure for Intermediate 2 using 4-fluoro-3-nitro-N,N-bis(2,2,2-trifluoroethyl)benzamide (200 mg, 0.574 mmol) and R-2-methylamino-1-Boc-piperidine (148 mg, 0.689 mmol) in 5 mL of EtOH containing Et₃N (0.160 mL, 1.14 mmol). The product was purified by flash chromatography on silica gel using 1:1/hexanes:EtOAc as eluent. Yield: 310 mg (99%); $^1$H NMR (CDCl$_3$) 1.47 (s, 9H), 1.55 (m, 1H), 1.74 (m, 5H), 2.80 (m, 1H), 3.37 (m, 1H), 3.65 (m, 1H), 4.10 (m, 1H), 4.27 (q, J=8.40 Hz, 4H), 4.64 (m, 1H), 7.07 (d, J=8.59 Hz, 1H), 7.55 (d, J=8.79 Hz, 1H), 8.31 (s, 1H), 8.39 (brs, 1H); MS (ESI) 443.35 (MH+-t-Boc).

Intermediate 14 tert-Butyl 3-{[(4-{[bis(2,2,2-trifluoroethyl)amino]carbonyl}-2-nitrophenyl)amino]methyl}morpholine-4-carboxylate

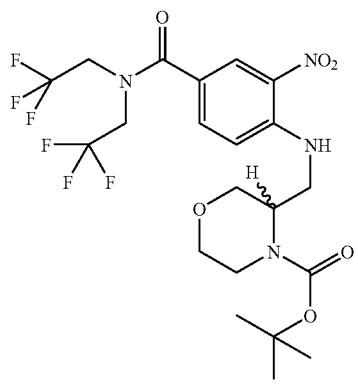

Following the general procedure for Intermediate 2 using 4-fluoro-3-nitro-N,N-bis(2,2,2-trifluoroethyl)benzamide (213 mg, 0.612 mmol) and tert-butyl 3-(aminomethyl)morpholine-4-carboxylate (160 mg, 0.734 mmol) in 10 mL of EtOH containing TEA (0.130 mL, 0.918 mmol). The product was purified by flash chromatography on silica gel using 2:1/hexanes:EtOAc as eluent. Yield: 304 mg (91%); $^1$H NMR (400 MHz, CHLOROFORM-D) δ 1.49 (s, 9H), 3.17 (m, 1H), 3.52 (m, 1H), 3.64 (m, 3H), 3.92 (m, 2H), 4.25 (q, J=8.20 Hz, 6H), 7.57 (d, J=8.59 Hz, 1H), 8.30 (d, J=1.95 Hz, 1H), 8.48 (m, 1H); MS (ESI) 544.75 (MH+).

Intermediate 15 tert-Butyl (2S)-2-{[(4-{[bis(2,2,2-trifluoroethyl)amino]carbonyl}-2-nitrophenyl)amino]methyl}piperidine-1-carboxylate

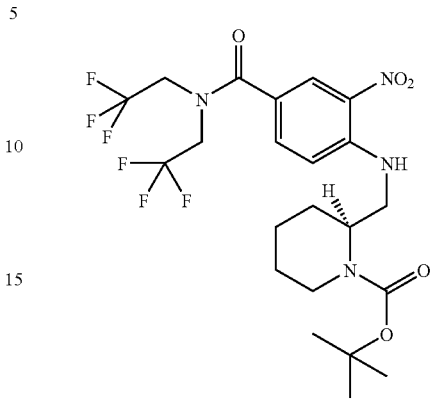

Following the general procedure for Intermediate 2 using 4-fluoro-3-nitro-N,N-bis(2,2,2-trifluoroethyl)benzamide (200 mg, 0.574 mmol) and tert-butyl (2S)-2-(aminomethyl)piperidine-1-carboxylate (150 mg, 0.689 mmol) in 10 mL of EtOH containing TEA (0.120 mL, 0.861 mmol). The product was purified by flash chromatography on silica gel using 3:1/hexanes:EtOAc as eluent Yield: 311 mg (99%); $^1$H NMR (400 MHz, CHLOROFORM-D) δ 1.47 (s, 9H), 1.52 (m, 1H), 1.66 (m, 1H), 1.71 (s, 2H), 1.74 (s, 2H), 2.79 (m, 1H), 3.36 (m, 1H), 3.65 (m, 1H), 4.09 (s, 1H), 4.26 (q, J=8.33 Hz, 4H), 4.64 (m, 1H), 7.07 (d, J=8.98 Hz, 1H), 7.55 (dd, J=8.89, 2.05 Hz, 1H), 8.30 (d, J=2.15 Hz, 1H), 8.39 (m, 1H); MS (ESI) 542.81 (MH+).

Intermediate 16

4-[(Cyclobutylmethyl)amino]-3-nitro-N,N-bis(2,2,2-trifluoroethyl)benzamide

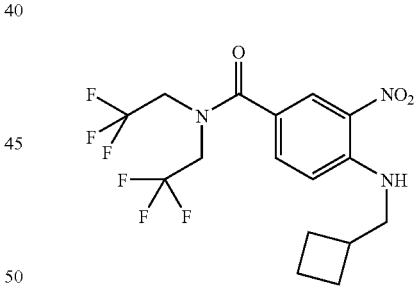

Following the general procedure for Intermediate 2 using 4-fluoro-3-nitro-N,N-bis(2,2,2-trifluoroethyl)benzamide (237 mg, 0.680 mmol) and cyclobutylmethyl amine (0.205 mL of a 4M/MeOH solution, 0.816 mmol) in 3 mL of EtOH containing TEA (0.140 mL, 1.02 mmol). The product was purified by flash chromatography on silica gel using 3:1/hexanes:EtOAc as eluent. Yield: 262 mg (93%); $^1$H NMR (400 MHz, CHLOROFORM-D) δ 1.83 (m, 2H), 1.97 (m, 1H), 2.02 (m, 1H), 2.20 (m, 2H), 2.73 (m, 1H), 3.37 (m, 2H), 4.27 (m, 4H), 6.93 (d, J=8.98 Hz, 1H), 7.53 (d, J=8.79 Hz, 1H), 8.24 (m, 1H), 8.30 (m, 1H); MS (ESI) 413.95 (MH+).

Intermediate 17

4-[(Cyclopentylmethyl)amino]-3-nitro-N,N-bis(2,2,2-trifluoroethyl)benzamide

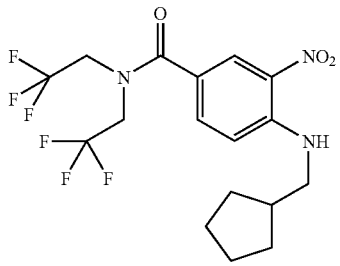

Following the general procedure for Intermediate 2 using 4-fluoro-3-nitro-N,N-bis(2,2,2-trifluoroethyl)benzamide (122 mg, 0.350 mmol) and cyclopentylmethyl amine (42 mg, 0.420 mmol) in 3 mL of EtOH containing TEA (0.075 mL, 0.525 mmol). The product was purified by flash chromatography on silica gel using 3:1/hexanes:EtOAc as eluent. Yield: 141 mg (94%); $^1$H NMR (400 MHz, CHLOROFORM-D) δ 1.30 (m, 2H), 1.64 (m, 4H), 1.89 (m, 2H), 2.26 (m, 1H), 3.24 (dd, J=7.23, 5.04 Hz, 2H), 4.23 (q, J=8.42 Hz, 4H), 6.91 (d, J=8.97 Hz, 1H), 7.50 (dd, J=8.97, 2.20 Hz, 1H), 8.26 (d, J=2.20 Hz, 1H), 8.33 (s, 1H); MS (ESI) 427.82 (MH+).

Intermediate 18

4-[(3-Furylmethyl)amino]-3-nitro-N,N-bis(2,2,2-trifluoroethyl)benzamide

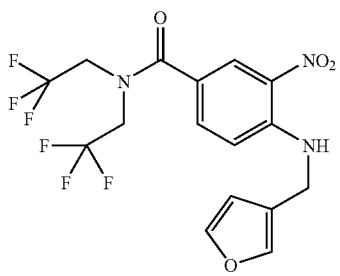

Following the general procedure for Intermediate 2 using 4-fluoro-3-nitro-N,N-bis(2,2,2-trifluoroethyl)benzamide (103 mg, 0.296 mmol) and 3-furylmethylamine (35 mg, 0.355 mmol) in 3 mL of EtOH containing TEA (0.060 mL, 0.444 mmol). The product was purified by flash chromatography on silica gel using 3:1/hexanes:EtOAc as eluent. Yield: 114 mg (91%); $^1$H NMR (400 MHz, CHLOROFORM-D) δ 4.26 (q, J=8.40 Hz, 4H), 4.44 (d, J=5.27 Hz, 2H), 6.43 (m, 1H), 7.00 (d, J=8.98 Hz, 1H), 7.46 (m, 2H), 7.55 (dd, J=8.88, 2.05 Hz, 1H), 8.32 (d, J=2.15 Hz, 1H), 8.45 (m, 1H); MS (ESI) 425.72 (MH+).

Intermediate 19

3-Nitro-4-[(3-thienylmethyl)amino]-N,N-bis(2,2,2-trifluoroethyl)benzamide

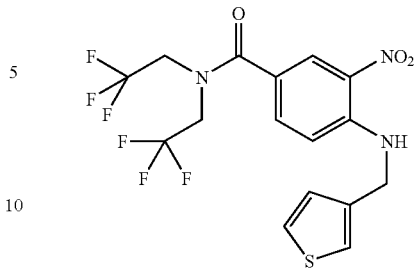

Following the general procedure for Intermediate 2 using 4-fluoro-3-nitro-N,N-bis(2,2,2-trifluoroethyl)benzamide (125 mg, 0.359 mmol) and 3-thienylmethylamine (49 mg, 0.431 mmol) in 3 mL of EtOH containing TEA (0.075 mL, 0.539 mmol).

The product was purified by flash chromatography on silica gel using 3:1/hexanes:EtOAc as eluent. Yield: 143 mg (90%); $^1$H NMR (400 MHz, CHLOROFORM-D) δ 4.24 (q, J=8.49 Hz, 4H), 4.59 (d, J=5.13 Hz, 2H), 6.95 (d, J=8.79 Hz, 1H), 7.07 (dd, J=5.04, 1.37 Hz, 1H), 7.22 (dd, J=3.02, 1.19 Hz, 1H), 7.37 (dd, J=5.04, 3.02 Hz, 1H), 7.51 (dd, J=8.61, 1.83 Hz, 1H), 8.31 (d, J=2.01 Hz, 1H), 8.60 (m, 1H); MS (ESI) 441.75 (MH+).

Intermediate 20

4-[[[(2R)-1-Methyl-2-pyrrolidinyl]methyl]amino]-3-nitro-N,N-bis(2,2,2-trifluoroethyl)-benzamide

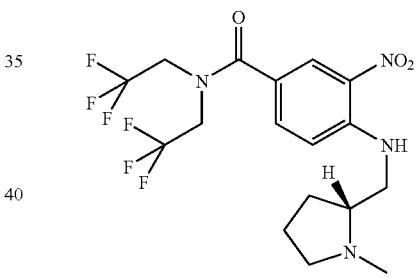

Intermediate 7 (167 mg, 0.308 mmol) was stirred in 2 mL of 1M HCl/AcOH at RT for 1 h. The solvent was evaporated. The residue was dissolved in THF (5 mL) and an excess of 37% HCHO/H$_2$O (1 mL) was added followed by NaBH(OAc)$_3$ (130 mg, 0.616 mmol). The solution was stirred at RT for 1 h. The solvent was concentrated. The residue was dissolved in EtOAc and washed with saturated NaHCO$_3$, brine and dried over anhydrous Na$_2$SO$_4$. The solvent was concentrated and the product was dried under vacuum to give the titled compound. Yield: 136 mg (99%); $^1$H NMR (CDCl$_3$) δ 1.69 (m, 2H), 1.81 (m, 1H), 2.01 (m, 1H), 2.28 (m, 1H), 2.35 (s, 3H), 2.58 (m, 1H), 3.15 (m, 1H), 3.32 (m, 2H), 4.21 (q, J=8.49 Hz, 4H), 6.88 (d, J=8.97 Hz, 1H), 7.49 (d, J=8.88 Hz, 1H), 8.26 (s, 1H), 8.61 (brs, 1H). MS (ESI) 443.95 (MH+).

Intermediate 21

3-Amino-4-[(3-methylbutyl)amino]-N,N-bis(2,2,2-trifluoroethyl)-benzamide

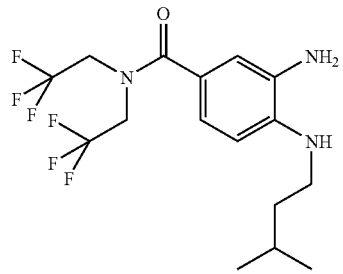

4-[(3-Methylbutyl)amino]-3-nitro-N,N-bis(2,2,2-trifluoroethyl)-benzamide (190 mg, 0.457 mmol) was dissolved in EtOAc (10 mL) containing a catalytic amount of 10% Pd/C. The solution was shaken with a Parr hydrogenation apparatus under H$_2$ atmosphere (40 psi) at RT overnight. The solution was filtered through diatomaceous earth and the solvent was concentrated giving the intermediate 21 as a white foam (176 mg, 99%); MS (ESI) 386.17 (MH+).

Intermediate 22

3-Amino-4-[[[(2R)-1-methyl-2-pyrrolidinyl]methyl]amino]-N,N-bis(2,2,2-trifluoroethyl)-benzamide

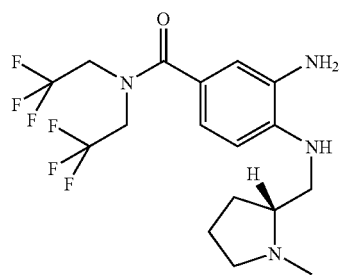

Following the same procedure as for Intermediate 21 using intermediate 20 (130 mg, 0.294 mmol) as starting material yielded the titled intermediate 16. Yield: 101 mg (85%); MS (ESI) 413.18 (MH+).

The synthesis of all other intermediates followed the same hydrogenation procedure as for Intermediate 21 giving the desired products in quantitative yields (to be included in Table 2).

TABLE 2

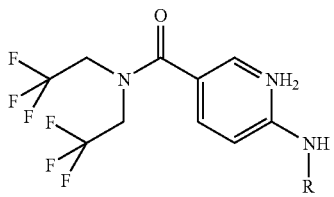

Intermediates prepared following a general procedure for Intermediate 21:

| Intermediates | R | (MH+) |
|---|---|---|
| Intermediate 23 | cyclopropylmethyl | 370.17 |
| Intermediate 24 | cyclohexylmethyl | 412.36 |
| Intermediate 25 | isobutyl | 396.25 |
| Intermediate 26 | (S)-N-Boc-pyrrolidin-2-ylmethyl | 499.44 |
| Intermediate 27 | (R)-N-Boc-pyrrolidin-2-ylmethyl | 499.44 |

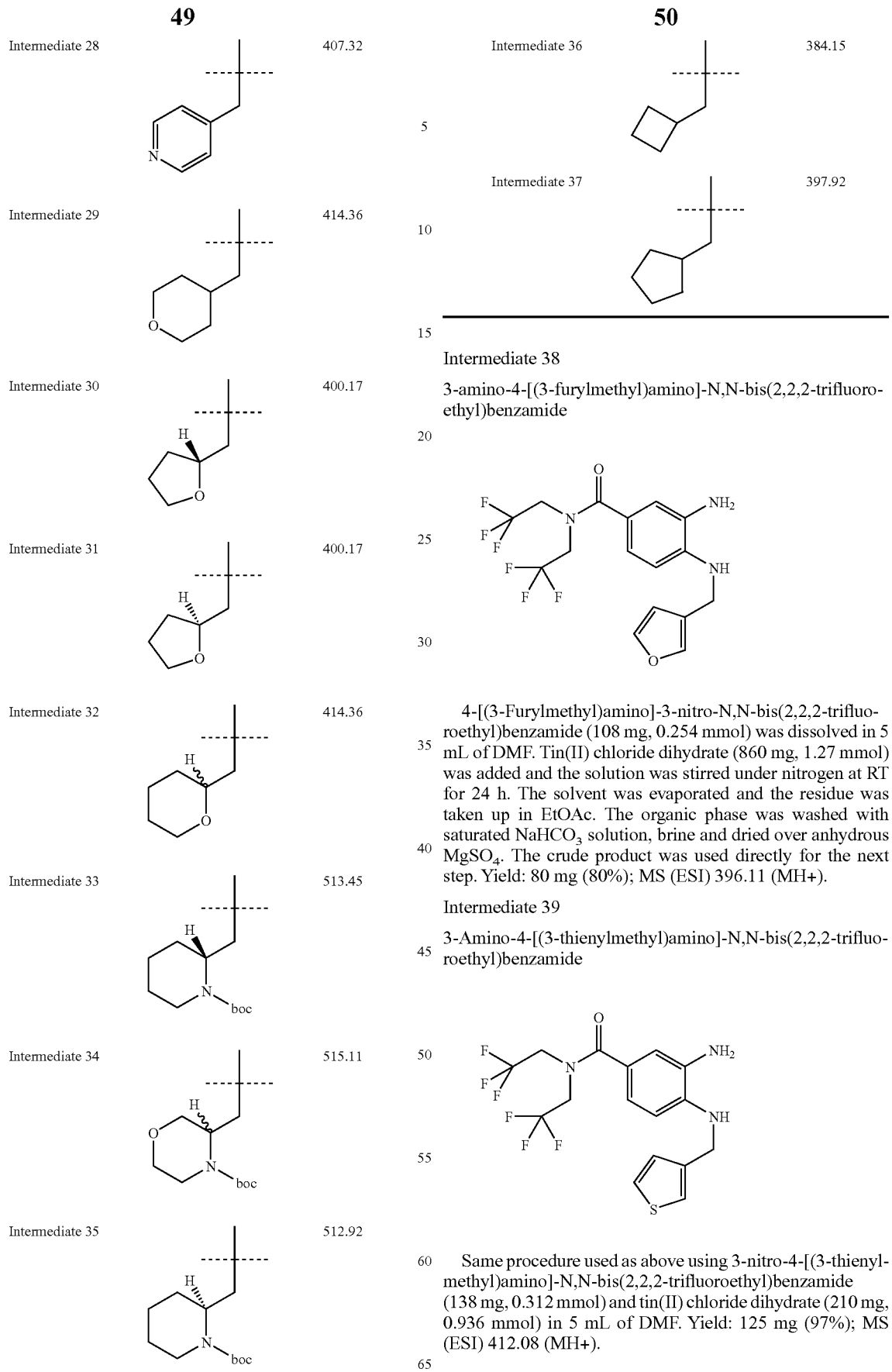

Intermediate 38

3-amino-4-[(3-furylmethyl)amino]-N,N-bis(2,2,2-trifluoroethyl)benzamide

4-[(3-Furylmethyl)amino]-3-nitro-N,N-bis(2,2,2-trifluoroethyl)benzamide (108 mg, 0.254 mmol) was dissolved in 5 mL of DMF. Tin(II) chloride dihydrate (860 mg, 1.27 mmol) was added and the solution was stirred under nitrogen at RT for 24 h. The solvent was evaporated and the residue was taken up in EtOAc. The organic phase was washed with saturated $NaHCO_3$ solution, brine and dried over anhydrous $MgSO_4$. The crude product was used directly for the next step. Yield: 80 mg (80%); MS (ESI) 396.11 (MH+).

Intermediate 39

3-Amino-4-[(3-thienylmethyl)amino]-N,N-bis(2,2,2-trifluoroethyl)benzamide

Same procedure used as above using 3-nitro-4-[(3-thienylmethyl)amino]-N,N-bis(2,2,2-trifluoroethyl)benzamide (138 mg, 0.312 mmol) and tin(II) chloride dihydrate (210 mg, 0.936 mmol) in 5 mL of DMF. Yield: 125 mg (97%); MS (ESI) 412.08 (MH+).

Example 3

2-[(4-Ethoxyphenyl)methyl]-1-3-methylbutyl)-N,N-bis(2,2,2-trifluoroethyl)-1H-benzimidazole-5-carboxamide

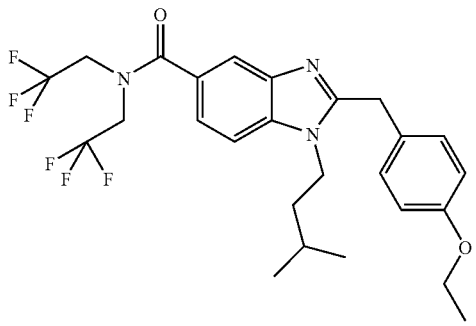

3-Amino-4-[(3-methylbutyl)amino]-N,N-bis(2,2,2-trifluoroethyl)-benzamide (176 mg, 0.457 mmol), 4-ethoxyphenylacetyl chloride (90 mg, 0.457 mmol) and zinc dust (30 mg, 0.457 mmol) were stirred in 1,2-dichloroethane (3 mL) at RT for 30 min. A catalytic amount of concentrated HCl (11.6 M) was added and the solution was stirred at 85° C. overnight. The solution was cooled to RT and diluted with dichloromethane. The organic phase was washed with saturated NaHCO$_3$ aqueous solution, brine and dried over anhydrous Na$_2$SO$_4$. The product was purified by reversed-phase HPLC using 20-80% CH$_3$CN/H$_2$O and then lyophilized affording the title compound as the corresponding TFA salt. Yield: 172 mg (71%); $^1$H NMR (CD$_3$OD) 0.90 (d, J=6.64 Hz, 6H), 1.35 (t, J=7.03 Hz, 3H), 1.61 (m, 1H), 4.00 (q, J=7.03 Hz, 2H), 4.23 (m, 2H), 4.39 (m, 6H), 6.90 (d, J=8.79 Hz, 2H), 7.20 (d, J=8.79 Hz, 2H), 7.44 (d, J=8.49 Hz, 1H), 7.66 (d, J=8.40 Hz, 1H), 7.75 (s, 1H); MS (ESI) 530.21 (MH+); Anal. Calcd. for C$_{26}$H$_{29}$N$_3$O$_2$F$_6$+0.3TFA+0.2H$_2$O: C, 56.31; H, 5.28; N, 7.41. Found: C, 56.29; H, 5.12; N, 7.48.

Example 4

1-(Cyclopropylmethyl)-2-[(4-ethoxyphenyl)methyl]-N,N-bis(2,2,2-trifluoroethyl)-1H-benzimidazole-5-carboxamide

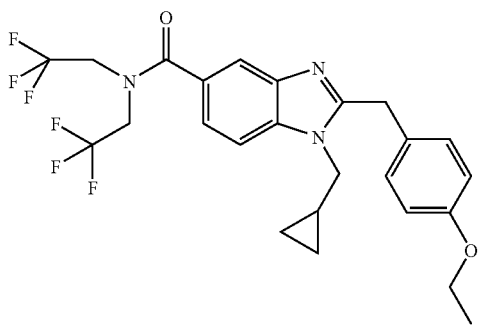

Following the general procedure in Example 3 using intermediate 23 (77 mg, 0.210 mmol), 4-ethoxyphenylacetyl chloride (42 mg, 0.210 mmol) and zinc dust (14 mg, 0.210 mmol) in 3 mL of 1,2-dichloroethane. The product was purified by reversed-phase HPLC using 20-80% CH$_3$CN/H$_2$O and then lyophilized affording the title compound as the corresponding TFA salt. Yield: 74 mg (73%); $^1$H NMR (CD$_3$OD) 0.47 (m, 2H), 0.63 (m, 2H), 1.27 (m, 1H), 1.38 (t, J=6.93 Hz, 3H), 4.02 (q, J=6.90 Hz, 2H), 4.37 (m, 6H), 4.56 (s, 2H), 6.97 (d, J=8.59 Hz, 2H), 7.28 (d, J=8.59 Hz, 2H), 7.60 (d, J=8.50 Hz, 1H), 7.79 (s, 1H), 8.00 (d, J=8.40 Hz, 1H); MS (ESI) 514.22 (MH+); Anal. Calcd. for C$_{25}$H$_{25}$N$_3$O$_2$F$_6$+1.0TFA+0.1H$_2$O: C, 51.53; H, 4.20; N, 6.68; Found: C, 51.49; H, 4.18; N, 6.55.

Example 5

1-(Cyclohexylmethyl)-2-[(4-ethoxyphenyl)methyl]-N,N-bis(2,2,2-trifluoroethyl)-1H-benzimidazole-5-carboxamide

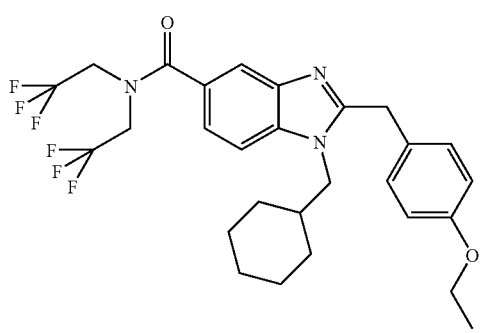

Following the general procedure in Example 3 using intermediate 24 (95 mg, 0.227 mmol), 4-ethoxyphenylacetyl chloride (50 mg, 0.250 mmol) and zinc dust (16 mg, 0.250 mmol) in 3 mL of 1,2-dichloroethane. The product was purified by reversed-phase HPLC using 20-80% CH$_3$CN/H$_2$O and then lyophilized affording the title compound as the corresponding TFA salt. Yield: 72 mg (48%); $^1$H NMR (CD$_3$OD) 1.12 (m, 5H), 1.36 (t, J=7.03 Hz, 3H), 1.58 (m, 2H), 1.69 (m, 4H), 4.02 (q, J=7.03 Hz, 2H), 4.23 (d, J=7.62 Hz, 2H), 4.36 (m, 4H), 4.50 (s, 2H), 6.94 (d, J=8.79 Hz, 2H), 7.24 (d, J=8.79 Hz, 2H), 7.56 (d, J=8.59 Hz, 1H), 7.76 (s, 1H), 7.90 (d, J=8.59 Hz, 1H); MS (ESI) 556.47 (MH+); Anal. Calcd. for C$_{28}$H$_{31}$N$_3$O$_2$F$_6$+0.9TFA+0.2H$_2$O; C, 54.09; H, 4.92; N, 6.35; Found: C, 54.12; H, 4.74; N, 6.20.

Example 6

2-[(4-Ethoxyphenyl)methyl]-1-(2-furanylmethyl)-N,N-bis(2,2,2-trifluoroethyl)-1H-benzimidazole-5-carboxamide

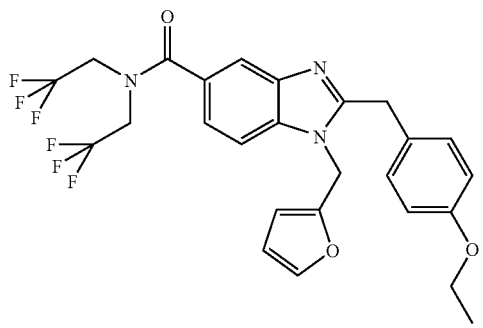

Following the general procedure in Example 3 using intermediate 25 (106 mg, 0.270 mmol), 4-ethoxyphenylacetyl chloride (59 mg, 0.297 mmol) and zinc dust (19 mg, 0.297 mmol) in 3 mL of 1,2-dichloroethane. The product was purified by reversed-phase HPLC using 20-80% $CH_3CN/H_2O$ and then lyophilized affording the title compound as the corresponding TFA salt. Yield: 78 mg (45%); $^1H$ NMR $(CD_3OD)$ 1.34 (t, J=7.03 Hz, 3H), 3.98 (q, J=7.03 Hz, 2H), 4.36 (m, 4H), 4.46 (s, 2H), 5.48 (s, 2H), 6.31 (m, 2H), 6.86 (d, J=8.79 Hz, 2H), 7.17 (d, J=8.79 Hz, 2H), 7.41 (m, 2H), 7.70 (s, 1H), 7.79 (d, J=8.59 Hz, 1H); MS (ESI) 540.38 (MH+); Anal. Calcd. for $C_{26}H_{23}N_3O_3F_6$+0.4TFA; C, 55.02; H, 4.03; N, 7.15. Found: C, 55.22; H, 4.21; N, 6.75.

Example 7

2-[(4-Ethoxyphenyl)methyl]-1-[(2S)-2-pyrrolidinylmethyl]-N,N-bis(2,2,2-trifluoroethyl)-1H-benzimidazole-5-carboxamide

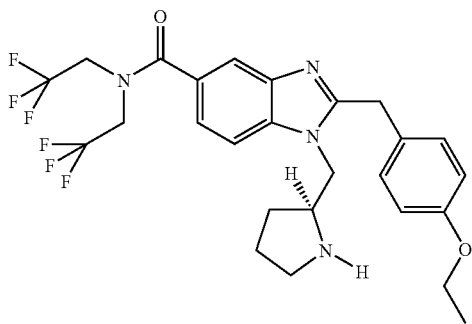

Following the general procedure in Example 3 using intermediate 27 (210 mg, 0.420 mmol), 4-ethoxyphenylacetyl chloride (85 mg, 0.420 mmol) and zinc dust (27 mg, 0.420 mmol) in 3 mL of 1,2-dichloroethane. The product was purified by reversed-phase HPLC using 10-50% $CH_3CN/H_2O$ and then lyophilized affording the title compound as the corresponding TFA salt. Yield: 95 mg (35%); $^1H$ NMR $(CD_3OD)$ 1.35 (t, J=7.03 Hz, 3H), 1.78 (m, 1H), 1.99 (m, 1H), 2.13 (m, 2H), 3.22 (m, 1H), 3.44 (m, 1H), 3.79 (m, 1H), 4.00 (q, J=7.03 Hz, 2H), 4.36 (m, 4H), 4.43 (s, 2H), 4.64 (d, J=6.84 Hz, 2H), 6.91 (d, J=8.79 Hz, 2H), 7.22 (d, J=8.79 Hz, 2H), 7.49 (d, J=8.49 Hz, 1H), 7.76 (m, 2H); MS (ESI) 543.44 (MH+); Anal. Calcd. for $C_{26}H_{28}N_4O_2F_6$+2.2TFA+0.3H$_2$O; C, 45.71; H, 3.89; N, 7.01. Found: C, 45.64; H, 3.74; N, 7.30.

Example 8

2-[(4-Ethoxyphenyl)methyl]-1-[(2R)-2-pyrrolidinylmethyl]-N,N-bis(2,2,2-trifluoroethyl)-1H-benzimidazole-5-carboxamide

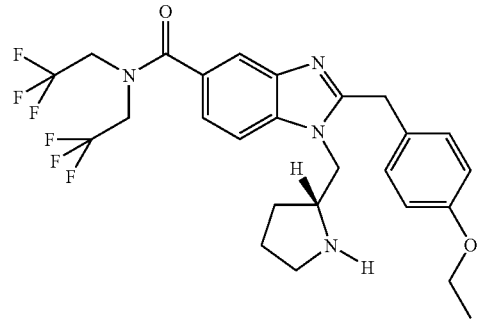

Following the general procedure in Example 3 using intermediate 26 (150 mg, 0.301 mmol), 4-ethoxyphenylacetyl chloride (60 mg, 0.301 mmol) and zinc dust (20 mg, 0.301 mmol) in 3 mL of 1,2-dichloroethane. The product was purified by reversed-phase HPLC using 10-50% $CH_3CN/H_2O$ and then lyophilized affording the title compound as the corresponding TFA salt. Yield: 83 mg (42%); $^1H$ NMR $(CD_3OD)$ 1.35 (t, J=7.03 Hz, 3H), 1.78 (m, 1H), 1.99 (m, 1H), 2.13 (m, 2H), 3.22 (m, 1H), 3.44 (m, 1H), 3.79 (m, 1H), 4.00 (q, J=7.03 Hz, 2H), 4.36 (m, 4H), 4.43 (s, 2H), 4.64 (d, J=6.84 Hz, 2H), 6.91 (d, J=8.79 Hz, 2H), 7.22 (d, J=8.79 Hz, 2H), 7.49 (d, J=8.49 Hz, 1H), 7.76 (s, 1H), 7.81 (d, J=8.40 Hz, 1H); MS (ESI) 543.44 (MH+); Anal. Calcd. for $C_{26}H_{28}N_4O_2F_6$+2.2TFA+0.4H$_2$O: C, 45.61; H, 3.90; N, 7.00. Found: C, 45.57; H, 3.74; N, 7.30.

Example 9

2-[(4-Ethoxyphenyl)methyl]-1-(4-pyridinylmethyl)-N,N-bis(2,2,2-trifluoroethyl)-1H-benzimidazole-5-carboxamide

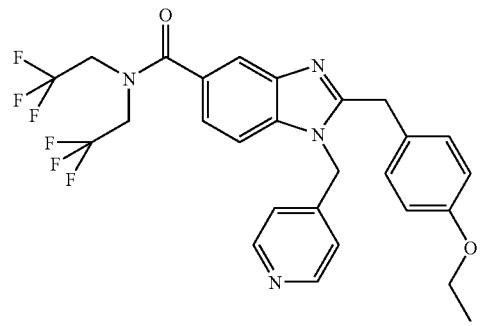

Following the general procedure in Example 3 using intermediate 28 (130 mg, 0.320 mmol), 4-ethoxyphenylacetyl chloride (70 mg, 0.352 mmol) and zinc dust (23 mg, 0.352 mmol) in 3 mL of 1,2-dichloroethane. The product was purified by reversed-phase HPLC using 10-50% CH₃CN/H₂O and then lyophilized affording the title compound as the corresponding TFA salt. Yield: 30 mg (15%); ¹H NMR (CD₃OD) 1.30 (t, J=7.03 Hz, 3H), 3.88 (q, J=7.03 Hz, 2H), 4.36 (m, 4H), 4.41 (s, 2H), 4.64 (d, J=6.84 Hz, 2H), 5.91 (s, 2H), 6.62 (d, J=8.40 Hz, 2H), 7.05 (d, J=8.59 Hz, 2H), 7.28 (d, J=5.66 Hz, 2H), 7.43 (d, J=8.40 Hz, 1H), 7.60 (d, J=8.40 Hz, 1H), 7.86 (s, 1H), 8.52 (brs, 2H); MS (ESI) 551.43 (MH+); Anal. Calcd. for C₂₇H₂₄N₄O₂F₆+2.5TFA; C, 46.00; H, 3.20; N, 6.71. Found: C, 46.17; H, 3.11; N, 6.63.

Example 10

2-[1-(4-Ethoxyphenyl)ethyl]-1-4-pyridinylmethyl)-N,N-bis(2,2,2-trifluoroethyl)-1H-benzimidazole-5-carboxamide

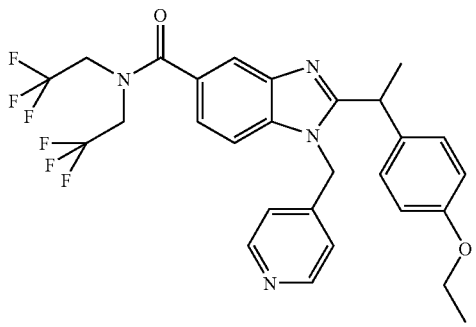

Following the general procedure in Example 3 using intermediate 28 (78 mg, 0.193 mmol), 4-ethoxy-□-methyl-phenylacetyl chloride (45 mg, 0.231 mmol) and zinc dust (15 mg, 0.231 mmol) in 3 mL of 1,2-dichloroethane. The product was purified by reversed-phase HPLC using 10-50% CH₃CN/H₂O and then lyophilized affording the title compound as the corresponding TFA salt. Yield: 16 mg (15%). ¹H NMR (CD₃OD) 1.29 (t, J=6.93 Hz, 3H), 1.77 (d, J=7.03 Hz, 3H), 3.85 (q, J=7.03 Hz, 2H), 4.37 (m, 5H), 4.50 (m, 1H), 5.67 (d, J=18.75 Hz, 1H), 5.82 (d, J=18.75 Hz, 1H), 6.56 (d, J=8.79 Hz, 2H), 6.96 (d, J=8.79 Hz, 2H), 7.05 (d, J=6.25 Hz, 1H), 7.34 (d, J=8.40 Hz, 1H), 7.46 (d, J=8.40 Hz, 1H), 7.86 (s, 1H), 8.40 (brs, 2H); MS (ESI) 565.43 (MH+); Anal. Calcd. for C₂₈H₂₆N₄O₂F₆+1.6TFA; C, 50.17; H, 3.72; N, 7.50. Found: C, 50.20; H, 3.71; N, 7.44.

Example 11

2-[(4-Ethoxyphenyl)methyl]-1-[(tetrahydro-2H-pyran-4-yl)methyl]-N,N-bis(2,2,2-trifluoroethyl)-1H-benzimidazole-5-carboxamide

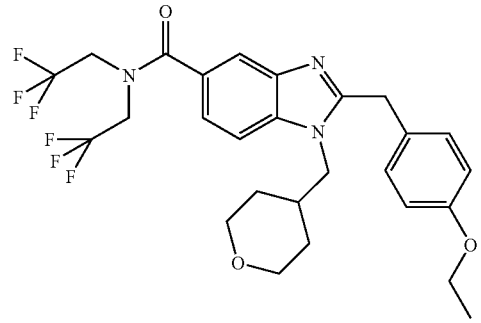

Following the general procedure in Example 3 using intermediate 29 (75 mg, 0.181 mmol), 4-ethoxyphenylacetyl chloride (40 mg, 0.199 mmol) and zinc dust (13 mg, 0.199 mmol) in 3 mL of 1,2-dichloroethane. The product was purified by reversed-phase HPLC using 10-60% CH₃CN/H₂O and then lyophilized affording the title compound as the corresponding TFA salt. Yield: 70 mg (58%). ¹H NMR (CD₃OD) 1.38 (t, J=7.03 Hz, 3H), 1.47 (m, 5H), 2.02 (m, 2H), 3.24 (m, 3H), 3.90 (m, 2H), 4.03 (q, J=7.03 Hz, 2H), 4.33 (d, J=7.62 Hz, 2H), 4.38 (m, 4H), 4.54 (s, 2H), 6.96 (d, J=8.59 Hz, 2H), 7.28 (d, J=8.59 Hz, 2H), 7.58 (d, J=8.49 Hz, 1H), 7.78 (s, 1H), 7.97 (d, J=8.40 Hz, 1H); MS (ESI) 558.48 (MH+); Anal. Calcd. for C₂₇H₂₉N₃O₃F₆+1.2TFA+0.2H₂O; C, 50.59; H, 4.42; N, 6.02. Found: C, 50.54; H, 4.47; N, 6.00.

Example 12

2-[(4-Ethoxyphenyl)methyl]-1-[[(2R)-tetrahydro-2-furanyl]methyl]-N,N-bis(2,2,2-trifluoroethyl)-1H-benzimidazole-5-carboxamide

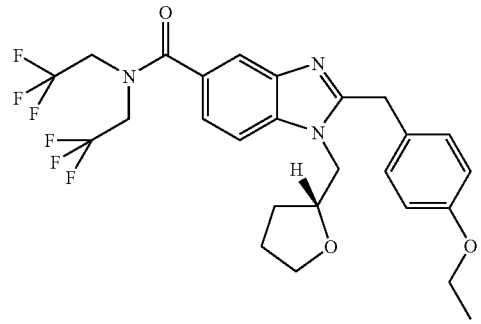

Following the general procedure in Example 3 using intermediate 30 (88 mg, 0.220 mmol), 4-ethoxyphenylacetyl chloride (48 mg, 0.242 mmol) and zinc dust (16 mg, 0.242 mmol) in 3 mL of 1,2-dichloroethane. The product was purified by reversed-phase HPLC using 10-60% CH₃CN/H₂O and then lyophilized affording the title compound as the corresponding TFA salt. Yield: 70 mg (50%). $^1$H NMR (CD$_3$OD) 1.38 (t, J=7.03 Hz, 3H), 1.74 (m, 1H), 1.97 (m, 2H), 2.18 (m, 1H), 3.72 (q, J=7.23 Hz, 1H), 3.91 (q, J=7.42 Hz, 1H), 4.03 (q, J=7.03 Hz, 2H), 4.21 (m, 1H), 4.36 (brs, 4H), 4.52 (m, 1H), 4.60 (s, 2H), 4.67 (m, 1H), 6.97 (d, J=8.40 Hz, 2H), 7.29 (d, J=8.40 Hz, 2H), 7.61 (d, J=8.59 Hz, 1H), 7.76 (s, 1H), 8.03 (d, J=8.59 Hz, 1H); MS (ESI) 544.45 (MH+); Anal. Calcd. for C$_{26}$H$_{27}$N$_3$O$_3$F$_6$+1.4TFA+0.2H$_2$O; C, 48.95; H, 4.11; N, 5.95. Found: C, 48.95; H, 3.93; N, 6.00.

Example 13

2-[(4-Ethoxyphenyl)methyl]-1-[[(2S)-tetrahydro-2-furanyl]methyl]-N,N-bis(2,2,2-trifluoroethyl)-1H-benzimidazole-5-carboxamide

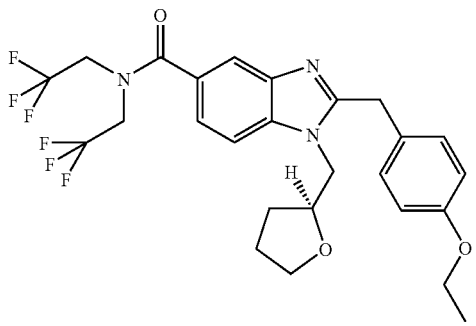

Following the general procedure in Example 3 using intermediate 31 (85 mg, 0.212 mmol), 4-ethoxyphenylacetyl chloride (46 mg, 0.233 mmol) and zinc dust (15 mg, 0.233 mmol) in 3 mL of 1,2-dichloroethane. The product was purified by reversed-phase HPLC using 10-60% CH$_3$CN/H$_2$O and then lyophilized affording the title compound as the corresponding TFA salt. Yield: 70 mg (50%). $^1$H NMR (CD$_3$OD) 1.38 (t, J=7.03 Hz, 3H), 1.74 (m, 1H), 1.95 (m, 2H), 2.18 (m, 1H), 3.72 (q, J=7.23 Hz, 1H), 3.91 (q, J=7.42 Hz, 1H), 4.03 (q, J=7.03 Hz, 2H), 4.21 (m, 1H), 4.38 (brs, 4H), 4.49 (m, 1H), 4.60 (s, 2H), 4.66 (d, 1H), 6.98 (d, J=8.40 Hz, 2H), 7.29 (d, J=8.40 Hz, 2H), 7.61 (d, J=8.59 Hz, 1H), 7.76 (s, 1H), 8.02 (d, J=8.59 Hz, 1H); MS (ESI) 544.45 (MH+); Anal. Calcd. for C$_{26}$H$_{27}$N$_3$O$_3$F$_6$+1.4TFA+0.1H$_2$O; C, 49.07; H, 4.09; N, 5.96. Found: C, 49.08; H, 4.05; N, 6.11.

Example 14

2-[(4-Ethoxyphenyl)methyl]-1-[(tetrahydro-2H-pyran-2-yl)methyl]-N,N-bis(2,2,2-trifluoroethyl)-1H-benzimidazole-5-carboxamide

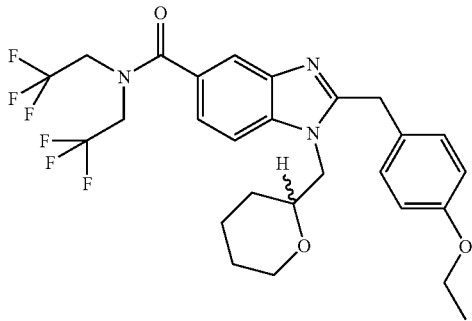

Following the general procedure in Example 3 using intermediate 32 (93 mg, 0.225 mmol), 4-ethoxyphenylacetyl chloride (49 mg, 0.248 mmol) and zinc dust (16 mg, 0.248 mmol) in 3 mL of 1,2-dichloroethane. The product was purified by reversed-phase HPLC using 10-60% CH$_3$CN/H$_2$O and then lyophilized affording the title compound as the corresponding TFA salt. Yield: 58 mg (38%). $^1$H NMR (CD$_3$OD) 1.38 (t, J=7.03 Hz, 3H), 1.42 (m, 1H), 1.51 (m, 3H), 1.80 (m, 1H), 1.90 (m, 1H), 3.23 (m, 1H), 3.59 (m, 1H), 3.89 (m, 1H), 4.04 (q, J=7.03 Hz, 2H), 4.30 (brs, 4H), 4.48 (m, 1H), 4.5 (s, 1H), 4.60 (d, J=8.59 Hz, 2H), 6.97 (d, J=8.79 Hz, 2H), 7.27 (d, J=8.59 Hz, 2H), 7.61 (d, J=8.59 Hz, 1H), 7.76 (s, 1H), 8.01 (d, J=8.59 Hz, 1H); MS (ESI) 558.53 (MH+); Anal. Calcd. for C$_{27}$H$_{29}$N$_3$O$_3$F$_6$+1.6TFA; C, 49.02; H, 4.17; N, 5.68. Found: C, 49.12; H, 4.05; N, 5.81.

Example 15

2-[(4-Ethoxyphenyl)methyl]-1-[(2R)-2-piperidinylmethyl]-N,N-bis(2,2,2-trifluoroethyl)-1H-benzimidazole-5-carboxamide

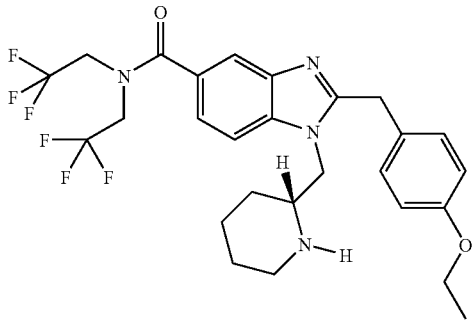

Following the general procedure in Example 3 using intermediate 33 (261 mg, 0.509 mmol), 4-ethoxyphenylacetyl chloride (101 mg, 0.509 mmol) and zinc dust (33 mg, 0.509 mmol) in 5 mL of 1,2-dichloroethane. The product was purified by reversed-phase HPLC using 10-60% CH$_3$CN/H$_2$O and then lyophilized affording the title compound as the corresponding TFA salt. Yield: 121 mg (35%). $^1$H NMR (CD$_3$OD) 1.37 (t, J=7.03 Hz, 3H), 1.45 (m, 1H), 1.58 (m, 1H), 1.65 (m, 1H), 1.88 (brd, 3H), 2.80 (m, 1H), 3.38 (m, 2H), 4.02 (q, J=7.03 Hz, 2H), 4.40 (m, 4H), 4.46 (s, 2H), 4.53 (m, 2H), 6.95 (d, J=8.79 Hz, 2H), 7.24 (d, J=8.79 Hz, 2H), 7.51 (d, J=8.40 Hz, 1H), 7.77 (s, 1H), 7.82 (d, J=8.40 Hz, 1H); MS (ESI) 557.47 (MH+); Anal. Calcd. for C$_{27}$H$_3$ON$_4$O$_2$F$_6$+2.1TFA+0.2H$_2$O; C, 46.87; H, 4.10; N, 7.01. Found: C, 46.80; H, 3.90; N, 7.18.

Example 16

2-[(5-Ethoxy-2-pyridyl)methyl]-1-[(tetrahydro-2H-pyran-4-yl)methyl]-N,N-bis(2,2,2-trifluoroethyl)-1H-benzimidazole-5-carboxamide

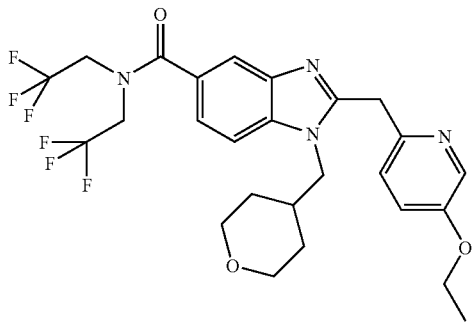

3-Amino-4-[[(tetrahydro-2H-pyran-4-yl)methyl]amino]-N,N-bis(2,2,2-trifluoroethyl)-benzamide (150 mg, 0.363 mmol), O-(7-azabenzotriazol-1-yl)-N,N,N'N'-tetramethyl uronium hexafluorophosphate (HATU) (151 mg, 0.399 mmol) and 5-ethoxy-2-pyridylacetic acid (72 mg, 0.399 mmol) were stirred in DMF (5 mL) containing diisopropylethylamine (DIPEA) (0.095 mL, 0.545 mmol) at RT for 3 h. The solvent was concentrated and the residue dissolved in EtOAc. The organic phase was washed with saturated aqueous NaHCO$_3$ solution, brine and dried over anhydrous Na$_2$SO$_4$. The solvent was concentrated and the product dissolved in 1,2-dichloroethane (3 mL). A catalytic amount of concentrated HCl (11.6M) was added and the solution was stirred at 85° C. for 3 h. The solvent was concentrated and the residue dissolved in EtOAc. The organic phase was washed with saturated NaHCO$_3$ solution, brine and dried over anhydrous Na$_2$SO$_4$. The product was purified by reversed-phase HPLC using 10-50% CH$_3$CN/H$_2$O and then lyophilized affording the title compound as the corresponding TFA salt. Yield: 131 mg (54%). $^1$H NMR (CD$_3$OD) 1.42 (t, J=7.03 Hz, 3H), 1.51 (m, 5H), 2.14 (m, 1H), 3.25 (m, 1H), 3.90 (d, J=10.94 Hz, 2H), 4.14 (q, J=7.03 Hz, 2H), 4.40 (m, 7H), 4.76 (m, 1H), 7.57 (m, 3H), 7.80 (s, 1H), 8.01 (d, J=8.59 Hz, 1H), 8.24 (s, 1H); MS (ESI) 559.48 (MH+); Anal. Calcd. for C$_{26}$H$_{28}$N$_4$O$_3$F$_6$+1.6TFA; C, 47.33; H, 4.03; N, 7.56. Found: C, 47.31; H, 4.08; N, 7.60.

Example 17

2-[(5-Ethoxy-2-pyridyl)methyl]-1-(3-methylbutyl)-N,N-bis(2,2,2-trifluoroethyl)-1H-benzimidazole-5-carboxamide

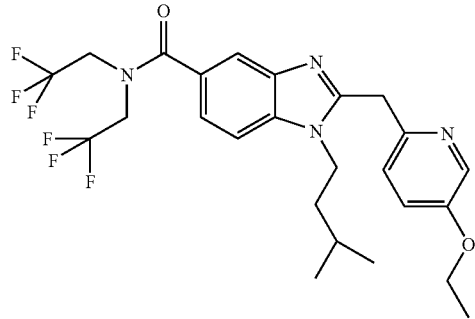

Following the general procedure in Example 16 using intermediate 21 (180 mg, 0.469 mmol), O-(7-azabenzotriazol-1-yl)-N,N,N'N'-tetramethyl uronium hexafluorophosphate (HATU) (196 mg, 0.516 mmol) and 5-ethoxy-2-pyridylacetic acid (93 mg, 0.516 mmol) were stirred in DMF (5 mL) containing diisopropylethylamine (DIPEA) (0.125 mL, 0.704 mmol) The product was purified by reversed-phase HPLC using 10-50% CH$_3$CN/H$_2$O and then lyophilized affording the title compound as the corresponding TFA salt. Yield: 208 mg (69%). $^1$H NMR (CD$_3$OD) 0.97 (d, J=6.44 Hz, 6H), 1.40 (t, J=7.03 Hz, 3H), 1.58 (m, 2H), 1.70 (m, 1H), 4.12 (q, J=7.03 Hz, 2H), 4.42 (m, 8H), 7.47 (m, 1H), 7.51 (d, J=8.59 Hz, 1H), 7.58 (d, J=8.59 Hz, 1H), 7.81 (s, 1H), 7.88 (d, J=8.59 Hz, 1H), 8.20 (s, 1H); MS (ESI) 531.48 (MH+); Anal. Calcd. for C$_{25}$H$_{28}$N$_4$O$_2$F$_6$+0.8TFA+0.1H$_2$O; C, 51.24; H, 4.69; N, 8.99. Found: C, 51.30; H, 4.63; N, 8.90.

Example 18

2-[(4-Ethoxyphenyl)methyl]-1-[[(2R)-1-methyl-2-pyrrolidinyl]methyl]-N,N-bis(2,2,2-trifluoroethyl)-1H-benzimidazole-5-carboxamide

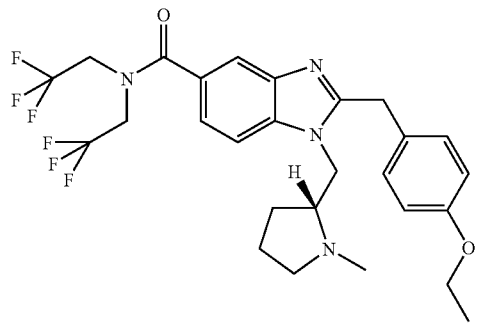

2-[[[2-Amino-4-[[bis(2,2,2-trifluoroethyl)amino]carbonyl]phenyl]amino]methyl]-(2R)-1-pyrrolidinecarboxylic acid-1,1-dimethylethyl ester (80 mg, 0.161 mmol), 4-ethoxyphenylacetyl chloride (32 mg, 0.161 mmol) and zinc dust (11 mg, 0.161 mmol) were stirred in 1,2-dichloroethane (3 mL) at RT for 30 min. A catalytic amount of concentrated HCl (11.6 M) was added and the solution was stirred at 85° C. overnight.

The solution was diluted with DCM and washed with saturated NaHCO$_3$ solution, brine and dried over anhydrous Na$_2$SO$_4$. The solvent was evaporated. The residue was dissolved in MeOH (3 mL) containing a few drops of acetic acid and 37% HCHO/H$_2$O (1 mL, excess) followed by NaCNBH$_3$ (12 mg, 0.193 mmol). The solution was stirred at RT for 1 h. The solvent was evaporated and the residue was dissolved in EtOAc. The organic phase was washed with saturated NaHCO$_3$ aqueous solution, brine and dried over anhydrous Na$_2$SO$_4$. The product was purified by reversed-phase HPLC using 10-50% CH$_3$CN/H$_2$O and then lyophilized affording the title compound as the corresponding TFA salt. Yield: 21 mg (20%); $^1$H NMR (CD$_3$OD) 1.36 (t, J=7.03 Hz, 3H), 1.82 (m, 1H), 2.01 (m, 2H), 2.94 (s, 3H), 3.18 (m, 1H), 3.72 (m, 1H), 3.79 (m, 1H), 4.00 (q, J=7.03 Hz, 2H), 4.38 (m, 4H), 4.43 (s, 2H), 4.57 (m, 1H), 4.79 (m, 1H), 6.92 (d, J=8.79 Hz, 2H), 7.21 (d, J=8.79 Hz, 2H), 7.46 (d, J=8.49 Hz, 1H), 7.76 (m, 2H); MS (ESI) 557.50 (MH+); Anal. Calcd. for C$_{27}$H$_3$ON$_4$O$_2$F$_6$+3.0TFA+0.9H$_2$O; C, 43.33; H, 3.83; N, 6.12. Found: C, 43.33; H, 3.75; N, 6.20.

Example 19

2-[(4-Ethoxyphenyl)methyl]-1-[[(2R)-1-methyl-2-piperidinyl]methyl]-N,N-bis(2,2,2-trifluoroethyl)-1H-benzimidazole-5-carboxamide

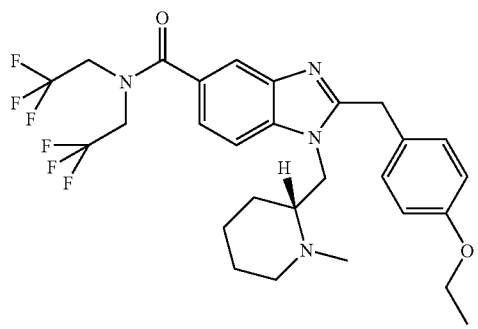

2-[(4-Ethoxyphenyl)methyl]-1-[(2R)-2-piperidinylmethyl]-N,N-bis(2,2,2-trifluoroethyl)-1H-benzimidazole-5-carboxamide (TFA salt) (50 mg, 0.637 mmol) was dissolved in 5 mL of THF containing a few drops of glacial acetic acid and an excess of 37% HCHO/H$_2$O (1 mL). NaBH(OAc)$_3$ (27 mg, 1.27 mmol) was added and the solution was stirred at RT for 1 h. The solvent was evaporated and the residue was dissolved in EtOAc. The organic phase was washed with saturated NaHCO$_3$ aqueous solution, brine and dried over anhydrous Na$_2$SO$_4$. The product was purified by reversed-phase HPLC using 10-50% CH$_3$CN/H$_2$O and then lyophilized affording the title compound as the corresponding TFA salt. Yield: 32 mg (74%); $^1$H NMR (CD$_3$OD) 1.20 (m, 1H), 1.36 (t, J=7.03 Hz, 3H), 1.44 (m, 1H), 1.72 (m, 2H), 1.86 (m, 1H), 2.95 (m, 1H), 3.03 (s, 3H), 3.24 (m, 1H), 3.57 (m, 1H), 4.01 (q, J=7.03 Hz, 2H), 4.39 (m, 7H), 6.92 (d, J=8.59 Hz, 2H), 7.21 (d, J=8.59 Hz, 2H), 7.44 (d, J=8.40 Hz, 1H), 7.68 (d, J=8.20 Hz, 1H), 7.76 (s, 1H); MS (ESI) 571.55 (MH+); Anal. Calcd. for C$_{28}$H$_{32}$N$_4$O$_2$F$_6$+1.5TFA+0.2H$_2$O; C, 49.96; H, 4.59; N, 7.52. Found: C, 49.97; H, 4.55; N, 7.59.

Example 20

2-[(5-Ethoxy-2-pyridyl)methyl]-1-[(2R)-2-pyrrolidinylmethyl]-N,N-bis(2,2,2-trifluoroethyl)-1H-benzimidazole-5-carboxamide

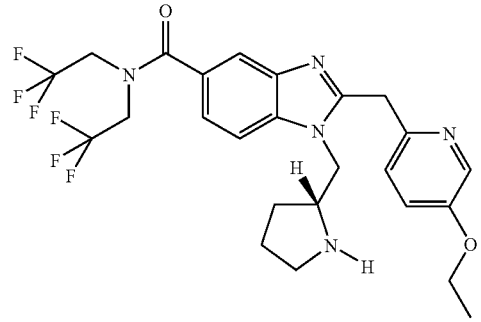

Following the general procedure in Example 16 using intermediate 26 (145 mg, 0.291 mmol), O-(7-azabenzotriazol-1-yl)-N,N,N',N'-tetramethyl uranium hexafluorophosphate (HATU) (125 mg, 0.320 mmol) and 5-ethoxy-2-pyridylacetic acid (60 mg, 0.320 mmol) were stirred in DMF (5 mL) containing diisopropylethylamine (DIPEA) (0.085 mL, 0.495 mmol). The product was purified by reversed-phase HPLC using 10-50% CH$_3$CN/H$_2$O and then lyophilized affording the title compound as the corresponding TFA salt. Yield: 96 mg (43%). $^1$H NMR (CD$_3$OD) 1.40 (t, J=7.03 Hz, 3H), 1.99 (m, 1H), 2.12 (m, 1H), 2.23 (m, 1H), 2.38 (m, 1H), 3.39 (m, 1H), 3.52 (m, 1H), 4.12 (q, J=7.03 Hz, 2H), 4.36 (m, 6H), 4.82 (m, 1H), 4.92 (m, 1H), 7.48 (d, J=8.59 Hz, 1H), 7.58 (m, 2H), 7.71 (s, 1H), 7.88 (d, J=8.40 Hz, 1H), 8.17 (s, 1H); MS (ESI) 544.45 (MH+); Anal. Calcd. for C$_{25}$H$_{27}$N$_5$O$_2$F$_6$+2.2TFA+0.2H$_2$O; C, 44.25; H, 3.74; N, 8.78. Found: C, 44.22; H, 3.77; N, 8.78.

Example 21

2-[14-Ethoxyphenyl)ethyl]-1-[(2R)-2-pyrrolidinylmethyl]-N,N-bis(2,2,2-trifluoroethyl)-1H-benzimidazole-5-carboxamide

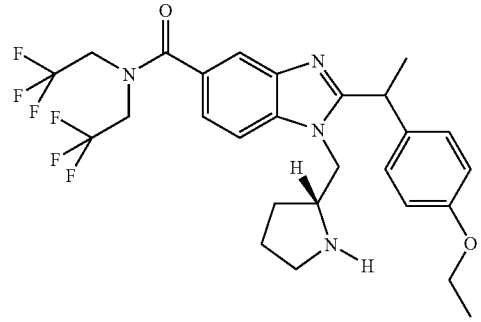

Following the general procedure in Example 3 using intermediate 26 (100 mg, 0.200 mmol), 4-ethoxyamethyl-phenylacetyl chloride (46 mg, 0.230 mmol) and zinc dust (15 mg, 0.231 mmol) in 3 mL of 1,2-dichloroethane. The product was purified by reversed-phase HPLC using 10-50% CH$_3$CN/H$_2$O and then lyophilized affording the title compound as the corresponding TFA salt. Yield: 25 mg (19%). $^1$H NMR (CD$_3$OD) 1.32 (t, J=7.03 Hz, 3H), 1.60 (m, 1H), 1.77 (d, J=7.03 Hz, 3H), 1.96 (m, 2H), 2.11 (m, 1H), 3.10 (m, 1H), 3.24 (m, 1H), 3.37 (m, 1H), 3.73 (m, 1H), 3.98 (q, J=7.03 Hz, 2H), 4.34 (m, 1H), 4.38 (m, 4H), 4.42 (m, 1H), 4.52 (m, 1H), 6.87 (d, J=8.40 Hz, 2H), 7.15 (m, 2H), 7.41 (d, J=8.40 Hz, 1H), 7.67 (d, J=8.40 Hz, 1H), 7.81 (s, 1H); MS (ESI) 557.49 (MH+).

Example 22

2-[(5-Ethoxy-2-pyridyl)methyl]-1-[[(2R)-1-methyl-2-piperidinyl]methyl]-N,N-bis(2,2,2-trifluoroethyl)-1H-benzimidazole-5-carboxamide

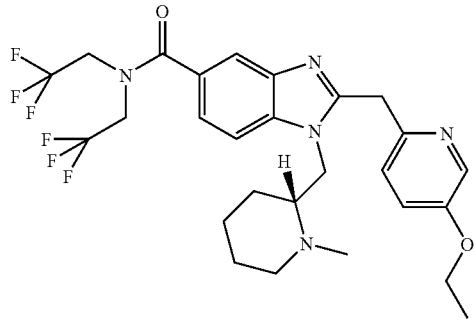

Intermediate 33 (135 mg, 0.263 mmol), HATU (120 mg, 0.315 mmol) and 5-ethoxy-2-pyridylacetic acid hydrochloride (70 mg, 0.315 mmol) were stirred in 5 mL of DMF containing DIPEA (0.095 mL, 0.526 mmol) at RT for 3 h. The solution was diluted with EtOAc and washed with saturated NaHCO$_3$ solution, brine and dried over anhydrous Na$_2$SO$_4$. The solvent was evaporated. The residue was dissolved in 3 mL of 1,2-dichloroethane containing a catalytic amount of concentrated HCl (11.6 M) and the solution was stirred at 80° C. for 5 h. The solution was cooled to RT and then diluted with dichloromethane. The solution was washed with saturated NaHCO$_3$ solution, brine and dried over anhydrous Na$_2$SO$_4$. The solvent was evaporated. The residue was dissolved in 5 mL of THF containing a catalytic amount of glacial acetic acid. An excess of 37% HCHO/H$_2$O (1 mL) was added followed by NaBH(OAc)$_3$ (68 mg, 0.316 mmol). The solution was stirred at RT for 1 h. The solution was then diluted with EtOAc and washed with saturated NaHCO$_3$ solution, brine and dried over anhydrous Na$_2$SO$_4$. The product was purified by reversed-phase HPLC using 10-50% CH$_3$CN/H$_2$O and lyophilized affording the title compound as the corresponding TFA salt. Yield: 53 mg (25%). $^1$H NMR (CD$_3$OD) 1.39 (t, J=7.03 Hz, 3H), 1.42 (m, 1H), 1.56 (m, 2H), 1.79 (m, 2H), 1.90 (m, 1H), 3.11 (brs, 4H), 3.60 (m, 1H), 3.80 (m, 1H), 4.12 (q, J=6.90 Hz, 2H), 4.36 (brd, 4H), 4.57 (m, 1H), 4.63 (m, 1H), 4.86 (m, 1H), 5.10 (m, 1H), 7.44 (d, J=8.40 Hz, 1H), 7.53 (s, 2H), 7.69 (s, 1H), 7.77 (d, J=8.40 Hz, 1H), 8.22 (s, 1H); MS ESI: 572.25 (MH+).

Example 23

2-[(5-Ethoxy-2-pyridyl)methyl]-1-[[(2R)-1-methyl-2-pyrrolidinyl]methyl]-N,N-bis(2,2,2-trifluoroethyl)-1H-benzimidazole-5-carboxamide

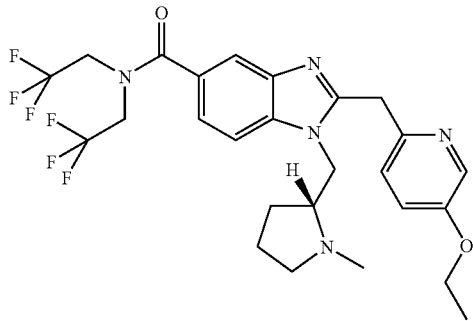

Intermediate 26 (101 mg, 0.245 mmol), HATU (112 mg, 0.294 mmol) and 5-ethoxy-2-pyridylacetic acid hydrochloride (65 mg, 0.294 mmol) were stirred in DMF (5 mL) containing DIPEA (0.090 mL, 0.490 mmol) at RT for 3 h. The solvent was evaporated. The residue was dissolved in EtOAc and washed with saturated NaHCO$_3$ solution, brine and dried over anhydrous Na$_2$SO$_4$. The solvent was evaporated and the residue was dissolve in 1,2-dichloroethane (3 mL). A catalytic amount of concentrated HCl (11.6 M) was added and the solution was then stirred at 80° C. for 5 h. The solution was cooled to RT and diluted with dichloromethane. The organic phase was washed with saturated NaHCO$_3$, brine and dried over anhydrous Na$_2$SO$_4$. The product was purified by reversed-phase HPLC using 10-50% CH$_3$CN/H$_2$O and then lyophilized affording the title compound as the corresponding TFA salt. Yield: 86 mg (45%); $^1$H NMR (CD$_3$OD) 1.39 (t, J=6.93 Hz, 3H), 1.98 (m, 1H), 2.15 (m, 2H), 2.29 (m, 1H), 2.86 (s, 3H), 3.32 (m, 1H), 3.85 (m, 1H), 4.12 (q, J=6.90 Hz, 2H), 4.19 (m, 1H), 4.36 (brs, 5H), 4.81 (m, 1H), 5.02 (m, 1H), 7.47 (d, J=8.50 Hz, 1H), 7.60 (m, 2H), 7.70 (s, 1H), 7.86 (d, J=8.59 Hz, 1H), 8.23 (s, 1H); MS (ESI) 558.19 (MH+).

Example 24

1-(Cyclobutylmethyl)-2-(4-ethoxybenzyl)-N,N-bis(2,2,2-trifluoroethyl)-1H-benzimidazole-5-carboxamide

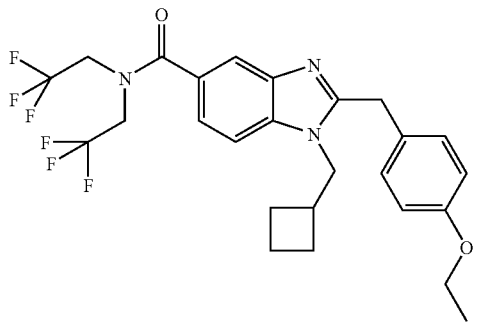

Following the general procedure in Example 16 using intermediate 36 (113 mg, 0.295 mmol), 4-ethoxyphenylacetic acid (58 mg, 0.325 mmol), HATU (123 mg, 0.325 mmol) and DIPEA (0.075 mL, 0.443 mmol) in 5 mL of DMF. The final dehydrated product was purified by reversed-phase HPLC using 20-80% CH₃CN/H₂O and then lyophilized affording the title compound as the corresponding TFA salt. Yield: 118 mg (62%); ¹H NMR (400 MHz, CD₃OD) δ 1.35 (t, J=6.84 Hz, 3H), 1.86 (m, 4H), 1.97 (m, 2H), 2.77 (m, 1H), 4.01 (q, J=7.03 Hz, 2H), 4.35 (m, 4H), 4.47 (d, J=7.03 Hz, 2H), 4.52 (s, 2H), 6.93 (d, J=8.59 Hz, 2H), 7.25 (d, J=8.59 Hz, 2H), 7.56 (d, J=8.59 Hz, 1H), 7.75 (s, 1H), 7.96 (d, J=8.40 Hz, 1H); MS (ESI) 528.1 (MH+); Anal. Calcd for $C_{26}H_{27}N_3O_2F_6$+0.6TFA+0.4H₂O: C, 54.17; H, 4.75; N, 6.97. Found: C, 54.08; H, 4.69; N, 6.96.

Example 25

1-(Cyclobutylmethyl)-2-[(5-ethoxypyridin-2-yl)methyl]-N,N-bis(2,2,2-trifluoroethyl)-1H-benzimidazole-5-carboxamide

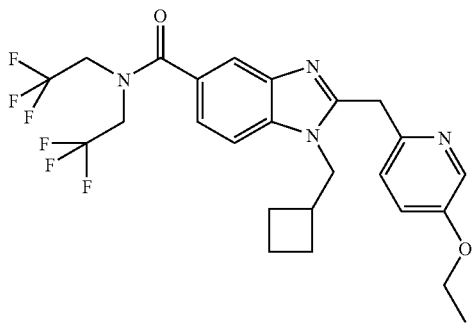

Following the general procedure in Example 16 using intermediate 36 (119 mg, 0.310 mmol), 5-ethoxy-2-pyridylacetic acid hydrochloride (75 mg, 0.341 mmol), HATU (130 mg, 0.341 mmol) and DIPEA (0.110 mL, 0.620 mmol) in 5 mL of DMF. The final dehydrated product was purified by reversed-phase HPLC using 20-80% CH₃CN/H₂O and then lyophilized affording the title compound as the corresponding TFA salt. Yield: 135 mg (68%); ¹H NMR (400 MHz, CD₃OD) δ 1.40 (t, J=7.03 Hz, 3H), 1.87 (m, 4H), 2.00 (m, 2H), 2.83 (m, 1H), 4.11 (q, J=6.96 Hz, 2H), 4.37 (brs, 4H), 4.51 (d, J=7.23 Hz, 2H), 4.72 (d, J=7.23 Hz, 2H), 7.50 (m, 2H), 7.57 (d, J=8.59 Hz, 1H), 7.78 (s, J=1H), 7.96 (d, J=8.40 Hz, 1H), 8.21 (d, J=2.54 Hz, 1H); MS (ESI) 529.1 (MH+); Anal. Calcd for $C_{25}H_{26}N_4O_2F_6$+1.5TFA+0.2H₂O: C, 47.83; H, 4.00; N, 7.97. Found: C, 47.80; H, 4.05; N, 7.93.

Example 26

1-(Cyclopentylmethyl)-2-[(5-ethoxypyridin-2-yl)methyl]-N,N-bis(2,2,2-trifluoroethyl)-1H-benzimidazole-5-carboxamide

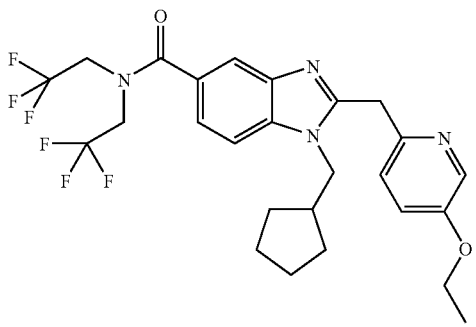

Following the general procedure in Example 16 using intermediate 37 (129 mg, 0.324 mmol), 5-ethoxy-2-pyridylacetic acid hydrochloride (78 mg, 0.356 mmol), HATU (135 mg, 0.356 mmol) and DIPEA (0.115 mL, 0.648 mmol) in 5 mL of DMF. The final dehydrated product was purified by reversed-phase HPLC using 20-80% CH₃CN/H₂O and then lyophilized affording the title compound as the corresponding TFA salt. Yield: 155 mg (73%); ¹H NMR (400 MHz, CD₃OD) δ 1.30 (m, 2H), 1.40 (t, J=6.83 Hz, 3H), 1.56 (m, 2H), 1.72 (m, 4H), 2.41 (m, 1H), 4.11 (q, J=7.03 Hz, 2H), 4.38 (m, 4H), 4.43 (d, J=7.81 Hz, 2H), 4.71 (s, 2H), 7.50 (s, 2H), 7.57 (d, J=8.79 Hz, 1H), 7.77 (s, 1H), 7.95 (d, J=8.59 Hz, 1H), 8.21 (s, 1H); MS (ESI) 543.1 (MH+); Anal. Calcd for $C_{26}H_{28}N_4O_2F_6$+1.1TFA: C, 50.71; H, 4.39; N, 8.39. Found: C, 50.76; H, 4.11; N, 8.36.

Example 27

2-(4-Ethoxybenzyl)-1-[(2S)-piperidin-2-ylmethyl]-N,N-bis(2,2,2-trifluoroethyl)-1H-benzimidazole-5-carboxamide

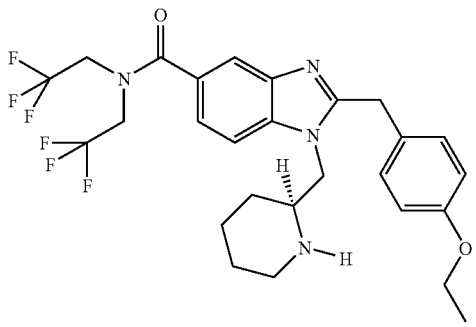

Following the general procedure in Example 16 using intermediate 35 (138 mg, 0.269 mmol), 4-ethoxyphenylacetic acid (53 mg, 0.296 mmol), HATU (112 mg, 0.296 mmol) and DIPEA (0.050 mL, 0.404 mmol) in 5 mL of DMF. The final dehydrated product was purified by reversed-phase HPLC using 10-50% CH₃CN/H₂O and then lyophilized affording the title compound as the corresponding TFA salt. Yield: 117 mg (65%); ¹H NMR (400 MHz, CD₃OD) δ 1.36 (t, J=6.83 Hz, 3H), 1.44 (m, 1H), 1.57 (m, 1H), 1.70 (m, 1H), 1.86 (m, 3H), 2.79 (m, 1H), 3.37 (m, 2H), 4.01 (q, J=7.03 Hz, 2H), 4.39 (m, 4H), 4.44 (s, 2H), 4.53 (m, 2H), 6.92 (d, J=8.79 Hz, 2H), 7.22 (d, J=8.79 Hz, 2H), 7.51 (d, J=8.29 Hz, 1H), 7.76 (s, 1H), 7.80 (d, J=8.40 Hz, 1H); MS (ESI) 557.1 (MH+).

Example 28

2-[(5-Ethoxypyridin-2-yl)methyl]-1-(3-furylmethyl)-N,N-bis(2,2,2-trifluoroethyl)-1H-benzimidazole-5-carboxamide

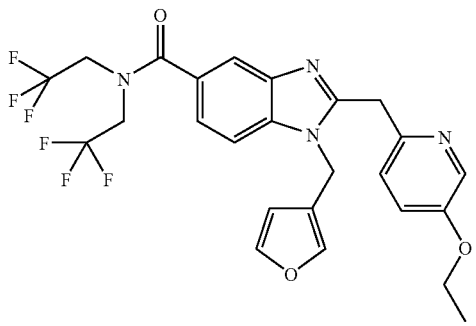

Following the general procedure in Example 16 using 3-amino-4-[(3-furylmethyl)amino]-N,N-bis(2,2,2-trifluoroethyl)benzamide (80 mg, 0.202 mmol), 5-ethoxy-2-pyridylacetic acid hydrochloride (48 mg, 0.222 mmol), HATU (85 mg, 0.222 mmol) and DIPEA (0.053 mL, 0.303 mmol) in 5 mL of DMF. The final dehydrated product was purified by reversed-phase HPLC using 20-80% CH₃CN/H₂O and then lyophilized affording the title compound as the corresponding TFA salt. Yield: 55 mg (42%); ¹H NMR (400 MHz, CD₃OD) δ 1.40 (t, J=7.03 Hz, 3H), 4.11 (q, J=7.03 Hz, 2H), 4.36 (m, 4H), 4.88 (s, 2H), 5.56 (s, 2H), 6.25 (s, 1H), 7.44 (s, 1H), 7.47 (s, 2H), 7.52 (m, 2H), 7.78 (s, 1H), 7.87 (d, J=8.59 Hz, 1H), 8.20 (s, 1H); MS (ESI) 541.1 (MH+); Anal. Calcd for C₂₅H₂₂N₄O₃F₆+1.2TFA+0.1H₂O: C, 48.46; H, 3.47; N, 8.25. Found: C, 48.50; H, 3.44; N, 8.27.

Example 29

2-[(5-Ethoxypyridin-2-yl)methyl]-1-(3-thienylmethyl)-N,N-bis(2,2,2-trifluoroethyl)-1H-benzimidazole-5-carboxamide

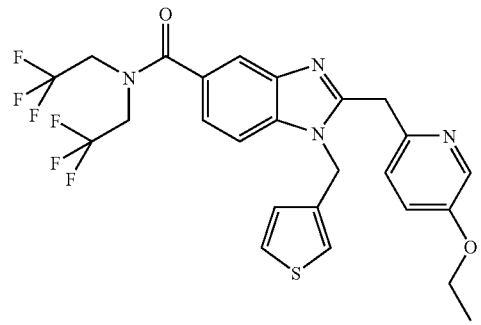

Following the general procedure in Example 16 using 3-amino-4-[(3-thienylmethyl)amino]-N,N-bis(2,2,2-trifluoroethyl)benzamide (125 mg, 0.303 mmol), 5-ethoxy-2-pyridylacetic acid hydrochloride (73 mg, 0.333 mmol), HATU (127 mg, 0.333 mmol) and DIPEA (0.105 mL, 0.606 mmol) in 5 mL of DMF. The final dehydrated product was purified by reversed-phase HPLC using 20-80% CH₃CN/H₂O and then lyophilized affording the title compound as the corresponding TFA salt. Yield: 137 mg (67%); ¹H NMR (400 MHz, CD₃OD) δ 1.38 (t, J=7.03 Hz, 3H), 4.07 (q, J=7.03 Hz, 2H), 4.36 (m, 4H), 4.90 (s, 2H), 5.65 (s, 2H), 6.86 (d, J=4.68 Hz, 1H), 7.14 (s, 1H), 7.38 (m, 3H), 7.45 (d, J=8.59 Hz, 1H), 7.73 (d, J=8.40 Hz, 1H), 7.77 (s, 1H), 8.12 (s, 1H); MS (ESI) 557.0 (MH+); Anal. Calcd for C₂₅H₂₂N₄O₂SF₆+0.7TFA+0.5H₂O: C, 49.13; H, 3.70; N, 8.68. Found: C, 49.08; H, 3.75; N, 8.65.

Example 30

1-(Cyclohexylmethyl)-2-[(5-ethoxypyridin-2-yl)methyl]-N,N-bis(2,2,2-trifluoroethyl)-1H-benzimidazole-5-carboxamide

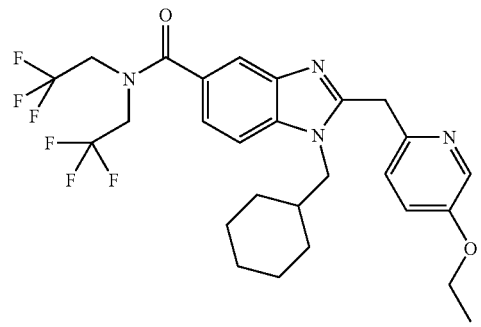

Following the general procedure in Example 16 using intermediate 24 (111 mg, 0.270 mmol), 5-ethoxy-2-pyridylacetic acid hydrochloride (65 mg, 0.297 mmol), HATU (113 mg, 0.297 mmol) and DIPEA (0.120 mL, 0.675 mmol) in 5 mL of DMF. The final dehydrated product was purified by reversed-phase HPLC using 20-80% $CH_3CN/H_2O$ and then lyophilized affording the title compound as the corresponding TFA salt. Yield: 109 mg (60%); $^1H$ NMR (400 MHz, $CD_3OD$) δ 1.12 (m, 5H), 1.38 (t, J=6.93 Hz, 3H), 1.59 (m, 2H), 1.60 (m, 1H), 1.68 (m, 2H), 1.78 (m, 1H), 4.10 (q, J=6.90 Hz, 2H), 4.28 (d, J=7.62 Hz, 2H), 4.36 (m, 4H), 4.70 (d, J=7.23 Hz, 1H), 4.88 (m, 1H), 7.50 (m, 2H), 7.55 (dd, J=1.37, 8.59 Hz, 1H), 7.77 (s, 1H), 7.93 (d, J=8.59 Hz, 1H), 8.20 (d, J=2.73 Hz, 1H); MS (ESI) 556.7 (MH+); Anal. Calcd for $C_{27}H_{30}N_4O_2F_6$+2.1TFA+0.1$H_2O$: C, 46.97; H, 4.08; N, 7.02. Found: C, 46.95; H, 4.12; N, 7.07.

Example 31

1-(Cyclohexylmethyl)-2-[(5-isopropoxypyridin-2-yl) methyl]-N,N-bis(2,2,2-trifluoroethyl)-1H-benzimidazole-5-carboxamide

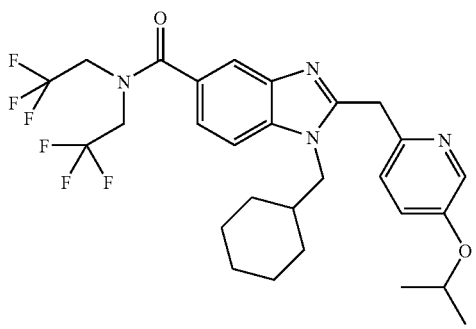

Following the general procedure in Example 16 using intermediate 24 (140 mg, 0.340 mmol), 4-isopropoxy-2-pyridylacetic acid hydrochloride.2LiCl (120 mg, 0.374 mmol), HATU (145 mg, 0.374 mmol) and DIPEA (0.175 mL, 1.02 mmol) in 5 mL of DMF. The final dehydrated product was purified by reversed-phase HPLC using 20-80% $CH_3CN/H_2O$ and then lyophilized affording the title compound as the corresponding TFA salt. Yield: 80 mg (35%); $^1H$ NMR (400 MHz, $CD_3OD$) δ 1.10 (m, 6H), 1.30 (d, J=6.05 Hz, 6H), 1.57 (m, 2H), 1.62 (m, 1H), 1.70 (m, 2H), 1.74 (m, 1H), 4.23 (d, J=7.62 Hz, 2H), 4.36 (m, 4H), 4.64 (m, 2H), 7.44 (s, 2H), 7.50 (dd, J=1.37, 8.40 Hz, 1H), 7.73 (s, 1H), 7.84 (d, J=8.59 Hz, 1H), 8.15 (s, 1H); MS (ESI) 571.2 (MH+); Anal. Calcd for $C_{28}H_{32}N_4O_2F_6$+0.6TFA+0.2$H_2O$: C, 54.58; H, 5.18; N, 8.72. Found: C, 54.55; H, 5.18; N, 8.67.

Example 32

2-(4-Ethoxybenzyl)-1-[(4-methylmorpholin-3-yl) methyl]-N,N-bis(2,2,2-trifluoroethyl)-1H-benzimidazole-5-carboxamide

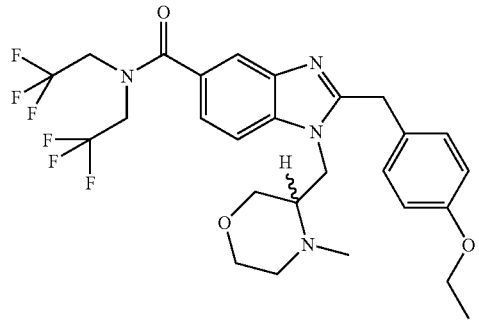

Following the general procedure in Example 22 using intermediate 34 (135 mg, 0.262 mmol), 4-ethoxyphenylacetic acid (57 mg, 0.314 mmol), HATU (120 mg, 0.314 mmol) and DIPEA (0.091 mL, 0.524 mmol) in 5 mL of DMF. The reductive amination step was performed using $NaBH(OAc)_3$ (111 mg, 0.525 mmol) in 5 mL of THF. The final product was purified by reversed-phase HPLC using 10-50% $CH_3CN/H_2O$ and then lyophilized affording the title compound as the corresponding TFA salt. Yield: 103 mg (57%); $^1H$ NMR (400 MHz, $CD_3OD$) δ 1.34 (t, J=7.03 Hz, 3H), 3.03 (s, 3H), 3.20 (m, 1H), 3.54 (m, 4H), 3.91 (m, 2H), 4.00 (q, J=7.03 Hz, 2H), 4.35 (m, 4H), 4.40 (s, 2H), 4.72 (m, 2H), 6.92 (d, J=8.59 Hz, 2H), 7.19 (d, J=8.79 Hz, 2H), 7.45 (d, J=8.40 Hz, 1H), 7.75 (m, 2H); MS (ESI) 573.2 (MH+); Anal. Calcd for $C_{27}H_{30}N_4O_3F_6$+1.8TFA: C, 47.25; H, 4.12; N, 7.20. Found: C, 47.22; H, 4.00; N, 7.44.

Example 33

2-[(5-Ethoxypyridin-2-yl)methyl]-1-[(4-methylmorpholin-3-yl)methyl]-N,N-bis(2,2,2-trifluoroethyl)-1H-benzimidazole-5-carboxamide

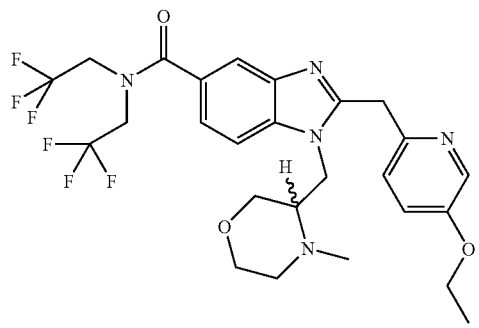

Following the general procedure in Example 22 using intermediate 34 (135 mg, 0.262 mmol), 5-ethoxy-2-pyridylacetic acid hydrochloride (68 mg, 0.314 mmol), HATU (120 mg, 0.314 mmol) and DIPEA (0.091 mL, 0.524 mmol) in 5 mL of DMF. The reductive amination step was performed by using $NaBH(OAc)_3$ (111 mg, 0.525 mmol) in 5 mL of THF. The final product was purified by reversed-phase HPLC using 10-50% CH₃CN/H₂O and then lyophilized affording the title compound as the corresponding TFA salt. Yield: 46 mg (26%); ¹H NMR (400 MHz, CD₃OD) δ 1.38 (t, J=7.03 Hz, 3H), 3.17 (s, 3H), 3.33 (m, 1H), 3.67 (m, 2H), 3.74 (m, 1H), 3.98 (m, 4H), 4.10 (q, J=7.03 Hz, 2H), 4.35 (brs, 4H), 4.98 (m, 2H), 7.43 (d, J=8.40 Hz, 1H), 7.51 (s, 2H), 7.68 (s, 1H), 7.78 (d, J=8.40 Hz, 2H), 8.21 (s, 1H); MS (ESI) 574.2 (MH+).

Example 34

2-(4-Ethoxybenzyl)-1-{[(2S)-1-methylpiperidin-2-yl]methyl}-N,N-bis(2,2,2-trifluoroethyl)-1H-benzimidazole-5-carboxamide

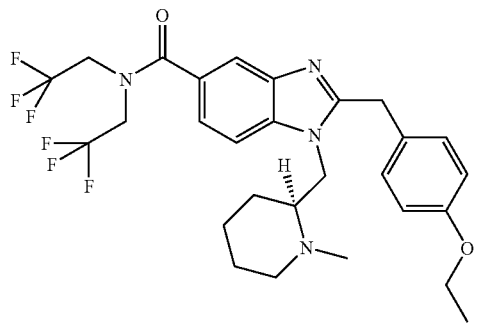

Following the general procedure in Example 22 using intermediate 35 (288 mg, 0.561 mmol), 4-ethoxyphenylacetic acid (120 mg, 0.673 mmol), HATU (255 mg, 0.673 mmol) and DIPEA (0.145 mL, 0.842 mmol) in 10 mL of DMF. The reductive amination step was performed by using NaBH(OAc)₃ (235 mg, 1.12 mmol) in 5 mL of THF. The final product was purified by reversed-phase HPLC using 10-50% CH₃CN/H₂O and then lyophilized affording the title compound as the corresponding TFA salt. Yield: 257 mg (67%); ¹H NMR (400 MHz, CD₃OD) δ 1.21 (m, 1H), 1.34 (t, J=6.93 Hz, 3H), 1.47 (m, 1H), 1.72 (m, 2H), 1.83 (m, 1H), 2.96 (m, 1H), 3.01 (s, 3H), 3.22 (m, 1H), 3.55 (m, 1H), 4.00 (q, J=7.03 Hz, 2H), 4.37 (m, 5H), 4.40 (s, 2H), 4.86 (m, 1H), 6.92 (d, J=8.59 Hz, 2H), 7.20 (d, J=8.59 Hz, 2H), 7.45 (d, J=8.40 Hz, 1H), 7.72 (m, 1H), 7.75 (s, 1H); MS (ESI) 571.2 (MH+); Anal. Calcd for C₂₈H₃₂N₄O₂F₆+1.8TFA+0.3H₂O: C, 47.07; H, 4.24; N, 6.78. Found: C, 47.03; H, 4.20; N, 6.93.

Example 35

2-(4-Isopropoxybenzyl)-1-{[(2R)-1-methylpiperidin-2-yl]methyl}-N,N-bis(2,2,2-trifluoroethyl)-1H-benzimidazole-5-carboxamide

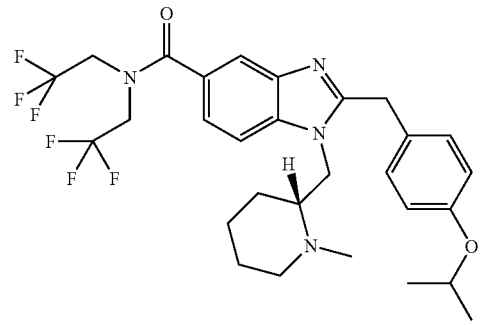

Following the general procedure in Example 22 using intermediate 33 (124 mg, 0.242 mmol), 4-isopropoxyphenylacetic acid (52 mg, 0.266 mmol), HATU (102 mg, 0.266 mmol) and DIPEA (0.065 mL, 0.363 mmol) in 5 mL of DMF. The reductive amination step was performed by using NaBH(OAc)₃ (105 mg, 0.484 mmol) in 5 mL of THF. The final product was purified by reversed-phase HPLC using 10-50% CH₃CN/H₂O and then lyophilized affording the title compound as the corresponding TFA salt. Yield: 112 mg (66%); ¹H NMR (400 MHz, CD₃OD) δ 1.19 (m, 1H), 1.26 (d, J=6.05 Hz, 6H), 1.34 (m, 1H), 1.45 (m, 1H), 1.70 (m, 2H), 1.81 (m, 1H), 2.96 (m, 1H), 3.01 (s, 3H), 3.56 (m, 1H), 4.36 (m, 5H), 4.40 (s, 2H), 4.56 (dt, J=6.05 Hz, 1H), 4.88 (m, 1H), 6.90 (d, J=8.79 Hz, 2H), 7.20 (d, J=8.79 Hz, 2H), 7.45 (dd, J=1.37, 8.59 Hz, 1H), 7.74 (m, 2H); MS (ESI) 585.2 (MH+); Anal. Calcd for C₂₉H₃₄N₄O₂F₆+2.3TFA+0.1H₂O: C, 47.55; H, 4.34; N, 6.60. Found: C, 47.51; H, 4.33; N, 6.74.

What is claimed is:

1. A compound of formula (I) or pharmaceutically acceptable salts thereof:

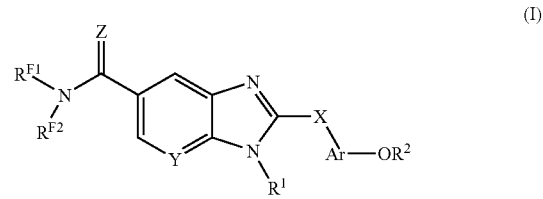

wherein

R^{F1} and R^{F2} are independently selected from —CF₃, —CH₂CF₃, —CH₂CHF₂, —CHFCF₃, —CHFCHF₂, —CHFCH₂F, —CF₂CF₃, —CF₂CH₃, —CF₂CH₂F, —CF₂CHF₂, —CF₃, —CH₂CCl₃, —CH₂CHCl₂, —CH₂CBr₃, —CH₂CHBr₃, —CH₂NO₂, —CH₂CH₂NO₂, —CH₂CN, —CH₂CH₂CN, and —CH₂CH₂OCH₃;

Z is selected from O= and S=;

R$^1$ is selected from C$_{1-10}$alkyl; C$_{1-10}$alkyl substituted by at least one of halogen, cyano, acetoxymethyl and nitro; C$_{2-10}$alkenyl; C$_{2-10}$alkenyl substituted by at least one of halogen, cyano, acetoxymethyl and nitro; C$_{2-10}$alkynyl; C$_{2-10}$alkynyl substituted by at least one of halogen, cyano, acetoxymethyl and nitro; R$^3$R$^4$N—C$_{1-6}$alkyl; R$^3$R$^4$NO(=O)—C$_{1-6}$alkyl; R$^3$O—C$_{1-6}$alkyl; R$^3$OC(=O)—C$_{1-6}$alkyl; R$^3$O(=O)—C$_{1-6}$alkyl; R$^3$O(=O)NR$^3$—C$_{1-6}$alkyl; R$^3$R$^4$NSO$_2$—C$_{1-6}$alkyl; R$^3$OSO$_2$N(R$^4$)—C$_{1-6}$alkyl; R$^3$R$^4$NO(=O)N(R$^5$)—C$_{1-6}$alkyl; R$^3$R$^4$NSO$_2$N(R$^5$)—C$_{1-6}$alkyl; aryl-C$_{1-6}$alkyl; aryl-O(=O)—C$_{1-6}$alkyl; heterocyclyl-C$_{1-6}$alkyl; heterocyclyl-O(=O)—C$_{1-6}$alkyl; substituted aryl-C$_{1-6}$alkyl; substituted aryl-O(=O)—C$_{1-6}$alkyl; substituted heterocyclyl-C$_{1-6}$alkyl; substituted heterocyclyl-O(=O)—C$_{1-6}$alkyl; and C$_{1-10}$hydrocarbylamino;

R$^2$ is selected from C$_{1-6}$alkyl, substituted C$_{1-6}$alkyl, C$_{2-6}$alkenyl, substituted C$_{2-6}$alkenyl, C$_{2-6}$alkynyl, substituted C$_{2-6}$alkynyl, C$_{3-6}$cycloalkyl, substituted C$_{3-6}$cycloalkyl, aryl, substituted aryl, and C$_{5-6}$heteroaryl, and substituted C$_{5-6}$heteroaryl;

R$^3$, R$^4$ and R$^5$ are independently selected from —H, C$_{1-6}$alkyl, C$_{2-6}$alkenyl, C$_{2-6}$alkynyl, and a divalent C$_{1-6}$ group that together with another divalent C$_{1-6}$ group forms a portion of a ring;

X is selected from —NR$^6$—, —C(=O)—, —CH$_2$—CH$_2$—, —CH=CH—, —O—, —C(R$^6$)(R$^7$)—, and —S(O)$_n$—, wherein n is 0, 1 or 2, wherein R$^6$ and R$^7$ are independently C$_{1-6}$alkyl, C$_{2-6}$alkenyl, C$_{2-6}$alkynyl, C$_{1-6}$alkoxy, —OH, or —H;

Ar is selected from an arylene; an heteroarylene; an arylene substituted by at least one group selected from C$_{1-6}$alkyl, halogen, trifluoromethyl, cyano, nitro, hydroxy and C$_{1-6}$alkoxy; and an heteroarylene substituted by at least one group selected from C$_{1-6}$alkyl, halogen, trifluoromethyl, cyano, nitro, hydroxy and C$_{1-6}$alkoxy; and Y is selected from —CH= and —N=.

2. The compound as claimed in claim 1, wherein Z is O=.

3. The compound as claimed in claim 1, wherein R$^1$ is selected from C$_{1-10}$alkyl; C$_{1-10}$alkyl substituted by at least one of halogen, cyano, acetoxymethyl and nitro; C$_{2-10}$alkenyl; C$_{2-10}$alkenyl substituted by at least one of halogen, cyano, acetoxymethyl and nitro; C$_{2-10}$alkynyl; C$_{2-10}$alkynyl substituted by at least one of halogen, cyano, acetoxymethyl and nitro; R$^3$R$^4$N—C$_{1-6}$alkyl; R$^3$R$^4$NC(=O)—C$_{1-6}$alkyl; R$_3$O—C$_{1-6}$ alkyl; R$^3$OC(=O)—C$_{1-6}$alkyl; R$^3$C(=O)—C$_{1-6}$alkyl; R$^3$C(=O)NR$^3$—C$_{1-6}$alkyl; R$^3$R$^4$NSO$_2$—C$_{1-6}$alkyl; R$^3$CSO$_2$N(R$^4$)—C$_{1-6}$alkyl; R$^3$R$^4$NC(=O)N(R$^5$)—C$_{1-6}$alkyl; R$^3$R$^4$NSO$_2$N(R$^5$)—C$_{1-6}$alkyl; aryl-C$_{1-6}$alkyl; aryl-C(=O)—C$_{1-6}$alkyl; heterocyclyl-C$_{1-6}$alkyl; heterocyclyl-C(=O)—C$_{1-6}$alkyl; substituted aryl-C$_{1-6}$alkyl; substituted aryl-C(=O)—C$_{1-6}$alkyl; substituted heterocyclyl-C$_{1-6}$alkyl; substituted heterocyclyl-C(=O)—C$_{1-6}$alkyl; and C$_{1-10}$hydrocarbylamino;

R$^2$ is selected from C$_{1-6}$alkyl, C$_{1-6}$alkyl substituted by at least one fluorine, C$_{2-6}$alkenyl, C$_{2-6}$alkenyl substituted by at least one fluorine, C$_{2-6}$alkynyl, C$_{2-6}$alkynyl substituted by at least one fluorine, C$_{3-6}$cycloalkyl, substituted C$_{3-6}$cycloalkyl, aryl, substituted aryl, and C$_{5-6}$heteroaryl, and substituted C$_{5-6}$heteroaryl;

R$^3$, R$^4$ and R$^5$ are independently selected from —H, C$_{1-6}$alkyl, C$_{2-6}$alkenyl, C$_{2-6}$alkynyl, and a divalent C$_{1-6}$ group that together with another divalent C$_{1-6}$ group forms a portion of a ring; and X is selected from —NR$^6$—, —C(=O)—, —CH$_2$—CH$_2$—, —OH =CH—, —O—, —C(R$^6$)(R$^7$)—, and —S(O)$_n$—, wherein n is 0, 1 or 2, wherein R$^6$ and R$^7$ are independently C$_{1-6}$alkyl, C$_{2-6}$alkenyl, C$_{2-6}$alkynyl, C$_{1-6}$alkoxy, —OH, or —H.

4. A compound according to claim 1,
wherein:
R$^1$ is selected from C$_{1-8}$alkyl; C$_{2-8}$alkenyl; C$_{2-8}$alkynyl; aryl-C$_{1-6}$alkyl; aryl-C$_{1-6}$alkyl with the aryl substituted by at least one group selected from C$_{1-6}$alkyl, acetoxymethyl, nitro and halogen; R$^8$R$^9$NC$_{1-6}$alkyl; R$^8$OC$_{1-6}$alkyl; cycloalkyl-C$_{1-6}$alkyl; heterocycloalkyl-C$_{1-6}$alkyl; heterocycloalkyl-C$_{1-6}$alkyl with the heterocycloalkyl thereof substituted by at least one group selected from C$_{1-8}$alkyl, acetoxymethyl, nitro and halogen; C$_{1-6}$alkylaryl; C$_{1-6}$alkyl—C(=O)—; C$_{6-8}$aryl—C(=O)—; C$_{4-8}$heteroaryl-C(=O)—; heteroaryl-C$_{1-6}$alkyl; heteroaryl-C$_{1-6}$alkyl with the heteroaryl thereof substituted by at least one group selected from C$_{1-6}$alkyl, acetoxymethyl, nitro and halogen; and R$^N$C$_{1-6}$alkyl;

R$^2$ is selected from —OH$_3$, —CH$_2$CH$_3$, —CH(CH$_3$)$_2$, C$_{3-6}$cycloalkyl, —CH$_2$CF$_3$, —CHF$_2$, —CF$_3$ and aryl;

R$^N$ is an oxidized pyridyl wherein the nitrogen atom on the pyridyl ring is in an oxidized state (N$^+$—O$^-$);

Ar is selected from an arylene; an heteroarylene; an arylene substituted by at least one group selected from C$_{1-6}$alkyl, halogen, trifluoromethyl, cyano, nitro, hydroxy and C$_{1-6}$alkoxy; and an heteroarylene substituted by at least one group selected from C$_{1-6}$alkyl, halogen, trifluoromethyl, cyano, nitro, hydroxy and C$_{1-6}$alkoxy; and R$^8$ and R$^9$ are independently selected from —H and C$_{1-6}$alkyl.

5. The compound according to claim 4,
wherein the arylene is para-arylene; and the heteroarylene is selected from six-membered ring para-heteroarylene and five-membered ring meta-heteroarylene.

6. A compound according to claim 1,
wherein:
R$^1$ is selected from ethyl, propyl, allyl, isopentyl, benzyl, dimethylaminoethyl, 4-pyridylmethyl, 2-pyridyl methyl, 1-pyrrolylethyl, cyclopropylmethyl, cyclobutylmethyl, cyclopentylmethyl, cyclohexylmethyl, 2-pyrrolidylmethyl, 3-pyrrolidylmethyl, N-methyl-2-pyrrolidylmethyl, N-methyl-3-pyrrolidylmethyl, 2-piperidylmethyl, 3-piperidylmethyl, 4-piperidylmethyl, N-methyl-2-piperidylmethyl, N-methyl-3-piperidylmethyl, N-methyl-4-piperidylmethyl, 3-thienylmethyl, 2-tetrahydrofuranylmethyl, 3-tetrahydrofuranylmethyl, 2-tetrahydropyranyl methyl, 3-tetrahydropyranylmethyl, 4-tetrahydropyranylmethyl, (2-nitrothiophene-5-yl)methyl, (1-methyl-1H-imidazole-2-yl)methyl, (5-(acetoxymethyl)-2-furanyl)methyl, (2,3-dihydro-1H-isoindole-1-yl)methyl, and 5-(2-methylthiazolyl);

R$^2$ is selected from —OH$_3$, —CH$_2$CH$_3$, —CH(CH$_3$)$_2$, —CH$_2$CF$_3$, OF$_3$, cyclopropyl, cyclobutyl, cyclopentyl, cyclohexyl and phenyl;

R$^{F1}$ and R$^{F2}$ are —CH$_2$CF$_3$ and Z is O=;

Ar is selected from a para-arylene; a para-arylene substituted with C$_{1-6}$alkyl, halogen, trifluoromethyl, cyano, nitro, hydroxy and C$_{1-6}$alkoxy; a six-membered ring para-heteroarylene; and a six-membered ring para-heteroarylene substituted with a group selected from C$_{1-6}$alkyl, halogen, trifluoromethyl, cyano, nitro, hydroxy and C$_{1-6}$alkoxy.

7. A compound according to claim 1,
wherein:
R$^{F1}$ and R$^{F2}$ are —CH$_2$CF$_3$, and Z is O=;
R$^2$ is —CH$_2$CH$_3$;

Ar is selected from para-phenylene and para-pyridylene; and

X is selected from —OH$_2$— and CH(CH$_3$)—.

8. A compound according to claim 1, wherein said compound is selected from:

2-[(4-Ethoxyphenyl)methyl]-1-(3-methylbutyl)-N,N-bis(2,2,2-trifluoroethyl)-1H-benzimidazole-5-carboxamide;

1-(Cyclopropylmethyl)-2-[(4-ethoxyphenyl)methyl]-N,N-bis(2,2,2-trifluoroethyl)-1H-benzimidazole-5-carboxamide;

1-(Cyclohexylmethyl)-2-[(4-ethoxyphenyl)methyl]-N,N-bis(2,2,2-trifluoroethyl)-1H-benzimidazole-5-carboxamide;

2-[(4-Ethoxyphenyl)methyl]-1-(2-furanylmethyl)-N,N-bis(2,2,2-trifluoroethyl)-1H-benzimidazole-5-carboxamide;

2-[(4-Ethoxyphenyl)methyl]-1-[(2S)-2-pyrrolidinylmethyl]-N,N-bis(2,2,2-trifluoroethyl)-1H-benzimidazole-5-carboxamide;

2-[(4-Ethoxyphenyl)methyl]-1-[(2R)-2-pyrrolidinylmethyl]-N,N-bis(2,2,2-trifluoroethyl)-1H-benzimidazole-5-carboxamide;

2-[(4-ethoxyphenyl)methyl]-1-(4-pyridinylmethyl)-N,N-bis(2,2,2-trifluoroethyl)-1H-benzimidazole-5-carboxamide;

2-[1-(4-Ethoxyphenyl)ethyl]-1-(4-pyridinylmethyl)-N,N-bis(2,2,2-trifluoroethyl)-1H-benzimidazole-5-carboxamide;

2-[(4-Ethoxyphenyl)methyl]-1-[(tetrahydro-2H-pyran-4-yl)methyl]-N,N-bis(2,2,2-trifluoroethyl)-1H-benzimidazole-5-carboxamide;

2-[(4-Ethoxyphenyl)methyl]-1-[[(2R)-tetrahydro-2-furanyl]methyl]-N,N-bis(2,2,2-trifluoroethyl)-1H-benzimidazole-5-carboxamide;

2-[(4-Ethoxyphenyl)methyl]-1-[[(2S)-tetrahydro-2-furanyl]methyl]-N,N-bis(2,2,2-trifluoroethyl)-1H-benzimidazole-5-carboxamide;

2-[(4-Ethoxyphenyl)methyl]-1-[(tetrahydro-2H-pyran-2-yl)methyl]-N,N-bis(2,2,2-trifluoroethyl)-1H-benzimidazole-5-carboxamide;

2-[(4-Ethoxyphenyl)methyl]-1-[(2R)-2-piperidinylmethyl]-N,N-bis(2,2,2-trifluoroethyl)-1H-benzimidazole-5-carboxamide;

2-[(5-Ethoxy-2-pyridyl)methyl]-1-[(tetrahydro-2H-pyran-4-yl)methyl]-N,N-bis(2,2,2-trifluoroethyl)-1H-benzimidazole-5-carboxamide;

2-[(5-Ethoxy-2-pyridinyl)methyl]-1-(3-methylbutyl)-N,N-bis(2,2,2-trifluoroethyl)-1H-benzimidazole-5-carboxamide;

2-[(4-Ethoxyphenyl)methyl]-1-[[(2R)-1-methyl-2-pyrrolidinyl]methyl]-N,N-bis(2,2,2-trifluoroethyl)-1H-benzimidazole-5-carboxamide;

2-[(4-Ethoxyphenyl)methyl]-1-[[(2R)-1-methyl-2-piperidinyl]methyl]-N,N-bis(2,2,2-trifluoroethyl)-1H-benzimidazole-5-carboxamide;

2-[(5-Ethoxy-2-pyridinyl)methyl]-1-[(2R)-2-pyrrolidinylmethyl]-N,N-bis(2,2,2-trifluoroethyl)-1H-benzimidazole-5-carboxamide;

2-[1-(4-Ethoxyphenyl)ethyl]-1-[(2R)-2-pyrrolidinylmethyl]-N,N-bis(2,2,2-trifluoroethyl)-1H-benzimidazole-5-carboxamide;

2-[(5-Ethoxy-2-pyridinyl)methyl]-1-[[(2R)-1-methyl-2-piperidinyl]methyl]-N,N-bis(2,2,2-trifluoroethyl)-1H-benzimidazole-5-carboxamide;

2-[(5-Ethoxy-2-pyridinyl)methyl]-1-[[(2R)-1-methyl-2-pyrrolidinyl]methyl]-N,N-bis(2,2,2-trifluoroethyl)-1H-benzimidazole-5-carboxamide;

1-(Cyclobutylmethyl)-2-(4-ethoxybenzyl)-N,N-bis(2,2,2-trifluoroethyl)-1H-benzimidazole-5-carboxamide;

1-(Cyclobutylmethyl)-2-[(5-ethoxypyridin-2-yl)methyl]-N,N-bis(2,2,2-trifluoroethyl)-1H-benzimidazole-5-carboxamide;

1-(Cyclopentylmethyl)-2-[(5-ethoxypyridin-2-yl)methyl]-N,N-bis(2,2,2-trifluoroethyl)-1H-benzimidazole-5-carboxamide;

2-(4-Ethoxybenzyl)-1-[(2S)-piperidin-2-ylmethyl]-N,N-bis(2,2,2-trifluoroethyl)-1H-benzimidazole-5-carboxamide;

2-[(5-Ethoxypyridin-2-yl)methyl]-1-(3-furylmethyl)-N,N-bis(2,2,2-trifluoroethyl)-1H-benzimidazole-5-carboxamide;

2-[(5-Ethoxypyridin-2-yl)methyl]-1-(3-thienylmethyl)-N,N-bis(2,2,2-trifluoroethyl)-1H-benzimidazole-5-carboxamide;

1-(Cyclohexylmethyl)-2-[(5-ethoxypyridin-2-yl)methyl]-N,N-bis(2,2,2-trifluoroethyl)-1H-benzimidazole-5-carboxamide;

1-(Cyclohexylmethyl)-2-[(5-isopropoxypyridin-2-yl)methyl]-N,N-bis(2,2,2-trifluoroethyl)-1H-benzimidazole-5-carboxamide;

2-(4-Ethoxybenzyl)-1-[(4-methylmorpholin-3-yl)methyl]-N,N-bis(2,2,2-trifluoroethyl)-1H-benzimidazole-5-carboxamide;

2-[(5-Ethoxypyridin-2-yl)methyl]-1-[(4-methylmorpholin-3-yl)methyl]-N,N-bis(2,2,2-trifluoroethyl)-1H-benzimidazole-5-carboxamide;

2-(4-Ethoxybenzyl)-1-{[(2S)-1-methylpiperidin-2-yl]methyl}-N,N-bis(2,2,2-trifluoroethyl)-1H-benzimidazole-5-carboxamide;

2-(4-Isopropoxybenzyl)-1-{[(2R)-1-methylpiperidin-2-yl]methyl}-N,N-bis(2,2,2-trifluoroethyl)-1H-benzimidazole-5-carboxamide;

and pharmaceutically acceptable salts thereof.

9. A pharmaceutical composition comprising a compound according to claim 1 and a pharmaceutically acceptable carrier.

10. A method for the therapy of pain in a warm-blooded animal, comprising the step of administering to said animal in need of such therapy a therapeutically effective amount of a compound according to claim 1.

11. A method of producing a compound of Formula (I) comprising the step of reacting a compound represented by formula (II) with R$^2$OArXCOA:

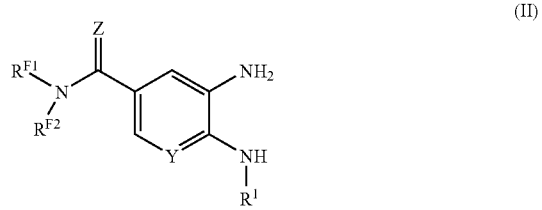

(II)

wherein

R$^{F1}$ and R$^{F2}$ are independently selected from —CF$_3$, —CH$_2$CF$_3$, —CH$_2$CHF$_2$, —CHFCF$_3$, —CHFCHF$_2$, —CHFCH$_2$F, —CF$_2$CF$_3$, —CF$_2$CH$_3$, —CF$_2$CH$_2$F, —CF$_2$CHF$_2$, —CF$_3$, —CH$_2$CCl$_3$, —CH$_2$CHCl$_2$, —CH₂CBr₃, —CH₂CHBr₃, —CH₂NO₂, —CH₂CH₂NO₂, —CH₂CN, —CH₂CH₂CN, and —CH₂CH₂OCH₃;

Z is selected from O= and S=;

$R^1$ is selected from $C_{1-10}$alkyl; $C_{1-10}$alkyl substituted by at least one of halogen, cyano, acetoxymethyl and nitro; $C_{2-10}$alkenyl; $C_{2-10}$alkenyl substituted by at least one of halogen, cyano, acetoxymethyl and nitro; $C_{2-10}$alkynyl; $C_{2-10}$alkynyl substituted by at least one of halogen, cyano, acetoxymethyl and nitro; $R^3R^4N$—$C_{1-6}$alkyl; $R^3R^4NC(=O)$—$C_{1-6}$alkyl; $R^3O$—$C_{1-6}$alkyl; $R^3OC(=O)$—$C_{1-6}$alkyl; $R^3C(=O)$—$C_{1-6}$alkyl; $R^3C(=O)NR^3$—$C_{1-6}$alkyl; $R^3R^4NSO_2$—$C_{1-6}$alkyl; $R^3OSO_2N(R^4)$—$C_{1-6}$alkyl; $R^3R^4NO(=O)N(R^5)$—$C_{1-6}$alkyl; $R^3R^4NSO_2N(R^5)$—$C_{1-6}$alkyl; aryl-$C_{1-6}$alkyl; aryl-O(=O)—$C_{1-6}$alkyl; heterocyclyl-$C_{1-6}$alkyl; heterocyclyl-O(=O)—$C_{1-6}$alkyl; substituted aryl-$C_{1-6}$alkyl; substituted aryl-O(=O)—$C_{1-6}$alkyl; substituted heterocyclyl-$C_{1-6}$alkyl; substituted heterocyclyl-O(=O)—$C_{1-6}$alkyl; and $C_{1-10}$hydrocarbylamino;

$R^2$ is selected from $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $C_{3-6}$cycloalkyl, substituted $C_{3-6}$cycloalkyl, aryl, substituted aryl, and $C_{5-6}$heteroaryl, and substituted $C_{5-6}$heteroaryl;

$R^3$, $R^4$ and $R^5$ are independently selected from —H, $C_{1-6}$alkyl, $C_{2-6}$alkenyl, $C_{2-6}$alkynyl, and a divalent $C_{1-6}$ group that together with another divalent $C_{1-6}$ group forms a portion of a ring;

X is selected from —$NR^6$—, —C(=O)—, —CH₂—CH₂—, —CH=CH—, —O—, —C($R^6$)($R^7$)—, and —S(O)$_n$—, wherein n is 0, 1 or 2, wherein $R^6$ and $R^7$ are independently $C_{1-6}$alkyl, $C_{2-6}$alkenyl, $C_{2-6}$alkynyl, $C_{1-6}$alkoxy, —OH, or —H;

A is selected from —OH, —Cl, —Br, and —I;

Ar is selected from an arylene: an heteroarylene: an arylene substituted by at least one group selected from $C_{1-6}$alkyl, halogen, trifluoromethyl, cyano, nitro, hydroxy and $C_{1-6}$alkoxy; and an heteroarylene substituted by at least one group selected from $C_{1-6}$alkyl, halogen, trifluoromethyl, cyano, nitro, hydroxy and $C_{1-6}$alkoxy; and Y is selected from CH= and N=.

12. A method of producing a compound of Formula (I) comprising the step of reacting a compound represented by formula (III) with formaldehyde:

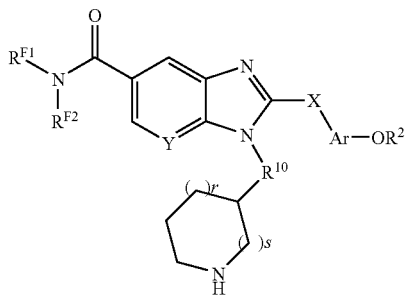

(III)

wherein r and s are selected from 0, 1 and 2;

$R^{10}$ is selected from $C_{1-6}$alkylene, —O—, and —$NR^{11}$—, wherein $R^{11}$ is a $C_{1-6}$alkyl;

$R^{F1}$ and $R^{F2}$ are independently selected from —CF₃, —CH₂CF₃, —CH₂CHF₂, —CHFCF₃, —CHFCHF₂, —CHFCH₂F, —CF₂CF₃, —CF₂CH₃, —CF₂CH₂F, —CF₂CHF₂, —CF₃, —CH₂CCl₃, —CH₂CHCl₂, —CH₂CBr₃, —CH₂CHBr₃, —CH₂NO₂, —CH₂CH₂NO₂, —CH₂CN, —CH₂CH₂CN, and —CH₂CH₂OCH₃;

X is selected from —$NR^6$—, —C(=O)—, —CH₂—CH₂—, —CH=CH—, —O—, —C($R^6$)($R^7$)—, and —S(O)$_n$—, wherein n is 0, 1 or 2, wherein $R^6$ and $R^7$ are independently $C_{1-6}$alkyl, $C_{2-6}$alkenyl, $C_{2-6}$alkynyl, $C_{1-6}$alkoxy, —OH, or —H;

Ar is selected from an arylene; an heteroarylene; an arylene substituted by at least one group selected from $C_{1-6}$alkyl, halogen, trifluoromethyl, cyano, nitro, hydroxy and $C_{1-6}$alkoxy; and an heteroarylene substituted by at least one group selected from $C_{1-6}$alkyl, halogen, trifluoromethyl, cyano, nitro, hydroxy and $C_{1-6}$alkoxy;

$R^2$ is selected from $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $C_{3-6}$cycloalkyl, substituted $C_{3-6}$cycloalkyl, aryl, substituted aryl, and $C_{5-6}$heteroaryl, and substituted $C_{5-6}$heteroaryl; and Y is selected from CH= and N=.

13. A pharmaceutical composition comprising a compound according to claim 6 and a pharmaceutically acceptable carrier.

14. A pharmaceutical composition comprising a compound according to claim 7 and a pharmaceutically acceptable carrier.

15. A pharmaceutical composition comprising a compound according to claim 8 and a pharmaceutically acceptable carrier.

16. A method for the therapy of pain in a warm-blooded animal, comprising the step of administering to said animal in need of such therapy a therapeutically effective amount of a compound according to claim 6.

17. A method for the therapy of pain in a warm-blooded animal, comprising the step of administering to said animal in need of such therapy a therapeutically effective amount of a compound according to claim 7.

18. A method for the therapy of pain in a warm-blooded animal, comprising the step of administering to said animal in need of such therapy a therapeutically effective amount of a compound according to claim 8.

* * * * *